US012570722B2

(12) United States Patent
Wright et al.

(10) Patent No.: US 12,570,722 B2
(45) Date of Patent: Mar. 10, 2026

(54) SINGLE ALPHA CHAIN COLLAGENS

(71) Applicant: Swansea University, Swansea (GB)

(72) Inventors: Chris Wright, Radyr (GB); Jonathan Widdowson, Neath (GB)

(73) Assignee: Swansea University, Swansea (GB)

( * ) Notice: Subject to any disclaimer, the term of this patent is extended or adjusted under 35 U.S.C. 154(b) by 0 days.

(21) Appl. No.: 18/384,018

(22) Filed: Oct. 26, 2023

(65) Prior Publication Data

US 2024/0052019 A1     Feb. 15, 2024

Related U.S. Application Data

(62) Division of application No. 16/754,095, filed as application No. PCT/GB2018/052913 on Oct. 11, 2018, now abandoned.

(30) Foreign Application Priority Data

Oct. 18, 2017    (GB) ..................................... 1717134

(51) Int. Cl.
    *C07K 14/78*        (2006.01)
    *A61K 38/39*        (2006.01)
(52) U.S. Cl.
    CPC .............. *C07K 14/78* (2013.01); *A61K 38/39* (2013.01)
(58) Field of Classification Search
    None
    See application file for complete search history.

(56) References Cited

FOREIGN PATENT DOCUMENTS

| CN | 101948533 A | 1/2011 |
| WO | WO 2017/122216 A1 | 7/2017 |
| WO | WO 2018/220396 A1 | 12/2018 |

OTHER PUBLICATIONS

Adachi et al., "Production of a Non-Triple Helical Collagen a Chain in Transgenic Silkworms and Its Evaluation as a Gelatin Substitute for Cell Culture," *Biotechnol Bioeng.* 106: 860-870, 2010.
Barrientos et al., "Electrospun Collagen-Based Nanofibres: A Sustainable Material for Improved Antibiotic Utilisation in Tissue Engineering Applications," *Int J Pharm.* 531:67-79, 2017.
"Collagen Protocol," https://www.abcam.com/protocols/collagen#collagen-extraction, downloaded Jan. 5, 2023, 8 pages.
Chandrakasan et al., "Preparation of Intact Monomeric Collagen from Rat Tail Tendon and Skin and the Structure of the Nonhelical Ends in Solution," *J Bio Chem.* 251:6062-6067, 1976.
Fleischmajer et al., "Rotary Shadowing of Collagen Monomers, Oligomers, and Fibrils During Tendon Fibrillogenesis," *J Histochem Cytochem.* 39:51-58, 1991.
Francois and Glimcher, "The Separation of the «-Chains of Collagen by Free-Flow Electrophoresis," *Biochem J.* 102:148-152, 1967.
Hattori et al., "Alkali-Treated Collagen Retained the Triple Helical Conformation and the Ligand Activity for the Cell Adhesion Via $\alpha 2\beta 1$ Integrin," *J Biochem* 125:676-684, 1999.
Kuznetsova et al. "Does the Triple Helical Domain of Type I Collagen Encode Molecular Recognition and Fiber Assembly while Telopeptides Serve as Catalytic Domains?," *J Biol Chem.* 274:36083-36088, 1999.
Liu et al., "Studies on collagen from the skin of channel catfish (*Ictalurus punctaus*)," *Food Chem.* 101:621-625, 2007.
PCT/GB2018/052913 Search Report and Written Opinion mailed on Jan. 3, 2019 (16 pages).
GB 1717134.9 Search Report dated Aug. 29, 2018 (5 pages).

*Primary Examiner* — Marsha Tsay
(74) *Attorney, Agent, or Firm* — Klarquist Sparkman, LLP

(57) ABSTRACT
The invention relates to a method for the production of single alpha chain collagens and an isolated or purified product comprising single alpha chain collagens.

11 Claims, 25 Drawing Sheets

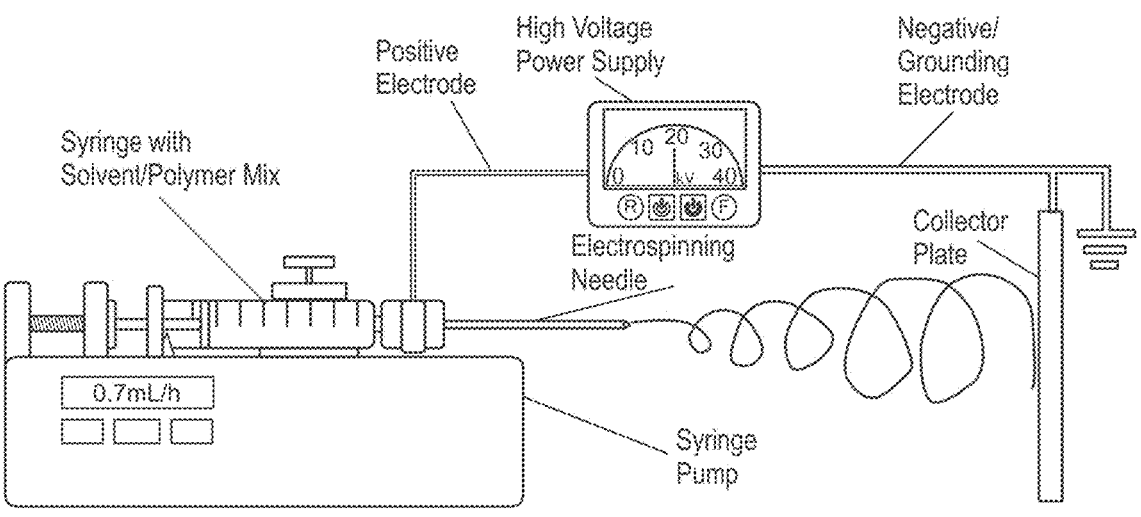

Figure 1

| Selection Of The Animal | Collagen Extraction | Freeze Drying | Storage | Age |
|---|---|---|---|---|
| Young and healthy animals contain fewer crosslinked collagen chains. This leads to an increase of soluble collagen. | Poor temperature control throughout extraction may render the collagen insoluble or convert to gelatin. | Poor heat and mass tranfer to and from the collagen could result in denaturation and/or crosslinking, reducing final material solubility. | Incorrect humidity or lighting could denature and/or crosslink the collagen, reducing solubility over time. | All Biomaterials have a natural expiration, and when left for prolonged periods can result in the breakdown of the molecule, denaturation and/or crosslinkng. |

Figure 2

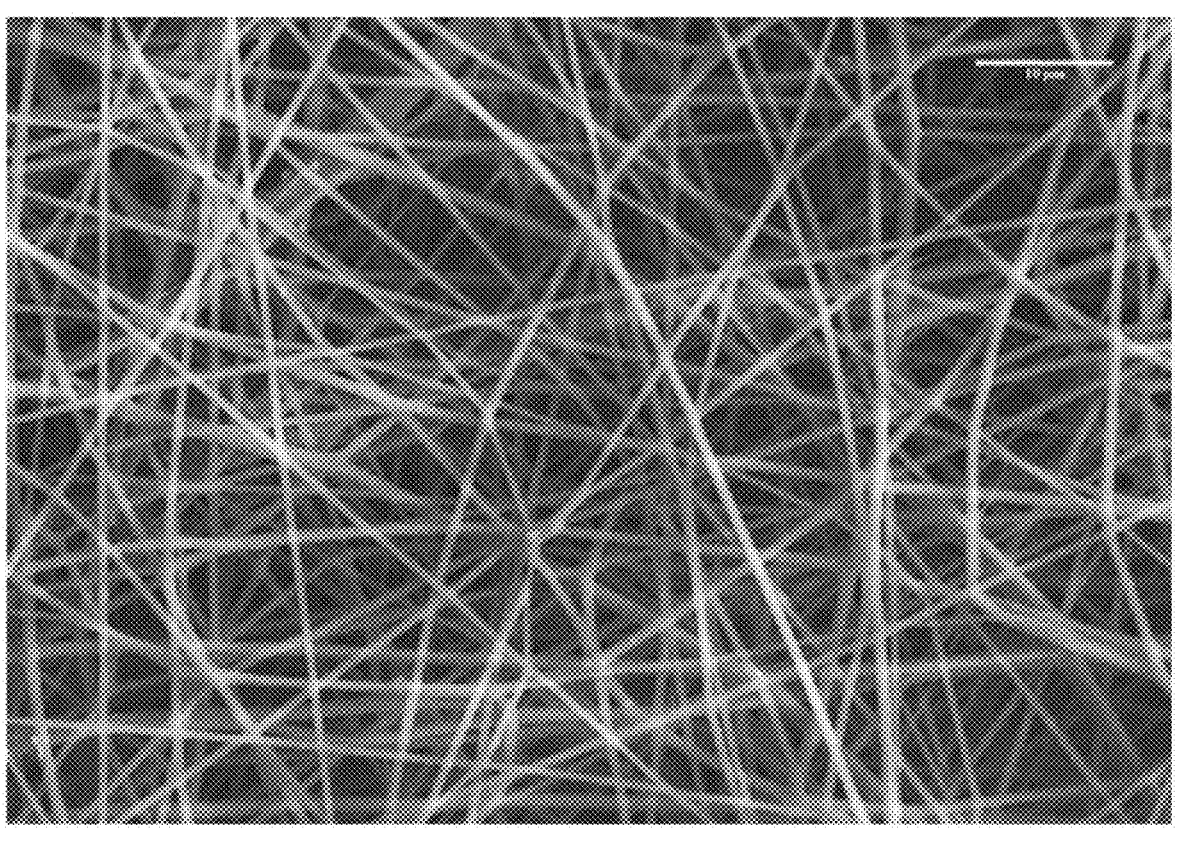
Figure 18A
Frequency of Range of Nanofibres (µm) - Jellyfish collagen
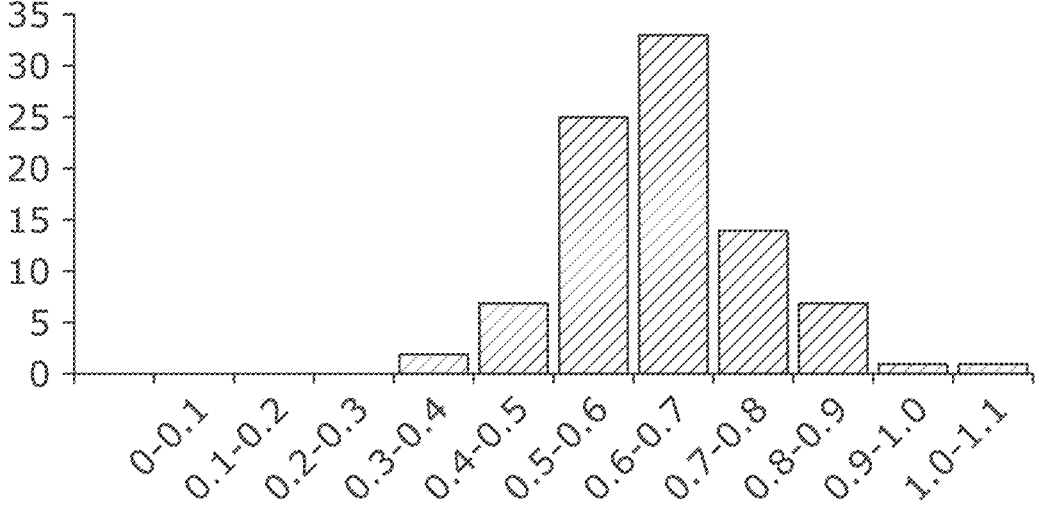
Figure 18B S4800 5.0kV 9.3mm x10.0k SE(M)      5.00um Frequency of Range of Nanofibres (nm) - PBS
Electrospun Jellyfish Collagen

SINGLE ALPHA CHAIN COLLAGENS

CROSS REFERENCE TO RELATED APPLICATIONS

This is a divisional of U.S. application Ser. No. 16/754, 095, filed Apr. 6, 2020, which is the U.S. National Stage of International Application No. PCT/GB2018/052913, filed Oct. 11, 2018, which was published in English under PCT Article 21(2), which in turn claims the benefit of Great Britain Application No. 1717134.9, filed Oct. 18, 2017. The prior US application and PCT applications are incorporated herein by reference in their entireties.

The invention relates to a method for the production of single, alpha chain collagens and an isolated or purified product comprising single alpha chain collagens.

BACKGROUND OF INVENTION

Collagens are the main group of structural proteins to be found in the extracellular matrix (ECM), and are the most abundant proteins found in animals, accounting for 25-35% of the whole body protein. Collagens all share a characteristic triple helix structure of Gly-X-Y repeats (where X can be any amino acid, and Y is often proline or hydroxyproline).

So far, 29 different Types of collagens have been classified (Brodsky B. et al; Kielty C. M. et al; Veit G. et al; and Shoulders M. D. et al) arising due to slight sequence differences in the primary structure. However, all collagens consist of three distinct polypeptide α-chains arranged in a triple helical conformation. The proper folding of each of these chains requires a glycine residue to be present at every third position in the polypeptide chain. The presence of proline or hydroxyproline in the Y position is also thought to contribute to the stability of the helical form. The individual chains are wound around one another to form a right handed superhelix rendering collagen fibres insoluble with high tensile strength.

Type I collagen is a heterotrimer comprising two α1 chains and one α2 chain.

When a tissue-extracted type I collagen sample is denatured and applied to SDS-PAGE, three regions are apparent on the gel: alpha, beta and gamma regions. The alpha region has a molecular weight of approximately 100 KDa, the beta region a molecular weight of approximately 200 KDa and the gamma region a molecular weight of approximately 300 KDA. The alpha region comprises two α1 and one α2 chains, per collagen molecule. The two α1 chains are overlain and produce more intense bands than the one α2 chain. The beta region comprises two combined α1 chains and a combined α1 and α2 chain; these two bands are overlapped on the gel. The gamma region comprises two α1 chains combined with one α2 chain. This is shown in FIG. 15. Thus, collagen contains a number of a chains that separate on SDS gels in a distinct manner.

Collagen proteins have wide ranging applications, such as the fabrication of scaffolds which are used in applications ranging from 3D cell culture and wound dressings to artificial tissue and organ production.

For collagen to be obtained in a usable form, it is typically extracted from a mammalian source but, more recently, it has been obtained from other sources such as Jellyfish. The standard procedure for obtaining a usable collagen mixture involves a technique of solubilisation in acetic acid (AcOH), which can be accompanied by pepsin treatment, where necessary, to aid in both the speed of extraction and yield of the resulting product. However, the use of pepsin in the process results in collagen which is lacking a significant amount of its telo-peptide region (collagen N- and C-terminal regions, or non-helical ends, important in fibril cross-linking and fibrillogenesis), often termed 'atelo collagen' which can affect its ability to form fibrils thus limiting its usefulness. These extraction processes have been adapted and modified in many ways, though yield has never been shown to rise above 2% from wet weight or 20% dry weight. Further, all extraction methods to date do not provide for the isolation of pure alpha chain collagen extract but rather they provide for alpha chains contaminated with other combined or helical forms of collagen (i.e. as seen as beta and, even more relevant, gamma regions on SDS gel) which can limit downstream utility, for example electrospinning.

Electrospinning of soluble collagens provides a suitable way of producing 3D scaffolds that closely mimic the high porosity and surface area often seen in the extra cellular matrix (ECM) of tissues. Thus, this fabrication process has been used in the production of scaffold devices for use in applications such as skin grafts and bone repair. The process of electrospinning uses a high voltage power supply to supply a positive charge to an electrospinning needle and a grounding electrode coupled to a collector plate (FIG. 1). The electrospinning needle comprises a syringe loaded with polymer and solvent, which is fed at a controlled rate using a syringe pump.

Research into collagen electrospinning has received extra attention in recent years due to the finding that the primary solvents used to electrospin collagen, namely 1,1,1,3,3,3 Hexafluoro-2-Propanol (HFP) and 2,2,2-Trifluoroethanol (TFE) have been shown to denature collagen. As a result many researchers now avoid electrospinning of both natural and synthetic polymer materials because of the reliance on aggressive solvents. There have been attempts to try and electrospin collagen, and other biopolymers, using benign solvent mixtures, however, many of these have been unable to replicate the prior success, in terms of fibre morphology and homogeneity, that collagen electrospun using HFP and TSE produces.

In addition to the concern about the use of solvents, the quality of the extracted collagen also affects how well the solution can be electrospun, for example, there are issues surrounding the electrospinning of gamma collagen, relating to the extraction conditions—these are critical issues that must be addressed. FIG. 2 shows how the collagen product can be influenced by a number of extraction conditions.

There is therefore a need for an alternative method of collagen extraction and preparation in order to obtain more stable and pure forms of collagen that are a faithful replication of the natural form and that lend themselves to subsequent manipulation, including, but not limited to, electrospinning.

We therefore herein disclose a novel collagen extraction technique that permits the isolation of pure single alpha chain (α1 & α2) collagens (SACCs) which hitherto has not been possible. These single collagen alpha chain isoforms are shown to be those chains that, importantly, undergo entanglement to form fibres during electrospinning, while the β and γ chains have a rigid structure which cannot form nanofibers. These SACCs have stable non-helical ends (or linear ends), often lost during the extraction techniques of the prior art, that also improve downstream utility. Moreover, the extracted collagen has also been found to be extremely soluble, even in benign solvents such as buffered solution, to an extent not remotely possible with less pure forms of collagen. This work also suggests that the increased solubility of the single alpha chain collagens aids electrospinning and prevents separation of insoluble collagen from solution.

We have shown that isolated SACCs can be electrospun preserving the nature of collagen's fibril forming abilities, while producing nanofiber scaffolds that are suitable for regenerative medicine and tissue engineering applications. We believe that the isolation of SACCs is extremely significant with wide spread application in the improved handling and application of collagen for the fabrication of medical and cosmetic materials.

STATEMENTS OF INVENTION

According to a first aspect or embodiment of the invention there is provided a method for the production or purification of single alpha chain collagens (SACCs) comprising:

a) obtaining an extraction of collagen in alkaline solution;

b) filtering the extraction using at least one first filter membrane to produce a first filter retentate;

c) adjusting the pH of the first filter retentate so that it is acidic thereby at least partially solubilising the collagen bound by same;

d) filtering the at least partially solubilised first filter retentate using said at least one first filter membrane to produce a second filter retentate;

e) adjusting the pH of the second filter retentate so that it is acidic thereby solubilising the collagen bound by same;

f) filtering the second filter retentate using at least one second filter membrane to produce a first filtrate comprising single alpha chain collagen; and g) optionally, filtering the first filtrate using said at least one first filter membrane to produce a second retentate comprising single alpha chain collagen.

Reference herein to retentate refers to the matter retained by the membrane and not allowed to pass through same.

Reference herein to collagen refers to a triple-helical structure based on a (Gly-Xaa-Yaa)n repeating sequence, such as any of the 28 types of collagens that so far have been described, including but not limited to: fibrillary type I collagen comprising two $\alpha1$ (I) chains and one $\alpha2$(I) chain; fibrillary type II collagen comprising three $\alpha1$ (II) chains and fibrillary type V collagen comprising three alpha chains (I, 11 and 111).

Reference herein to single alpha chain collagen (SAC) is reference to $\alpha1$ and $\alpha2$ chains i.e. single $\alpha1$ chain or single $\alpha2$ chain. Further, in the context of collagen type V, this may also further include an $\alpha3$ chain. As will be appreciated by those skilled in the art, typically $\alpha1$ and $\alpha2$ chains are formed during translation on ribosomes along the rough endoplasmic reticulum inside the cell (known as preprocollagen), and form an alpha helix having non-helical ends. However, preprocollagen undergoes cellular processing wherein non-helical ends are cleaved, along with hydroxylation and glycosylation of various amino acids of the alpha chains, leading to formation of what are known as alpha chain propeptides, which then further twist into a triple helix forming procollagen. This process is typically rapid. However, according to the present invention we have isolated these single alpha helix chains from the helix of triple helical collagen, which comprise intact non-helical ends that facilitate re-fibrillation back to triple helix under defined conditions.

In a preferred embodiment of the invention, the first filter membrane preferably has a Nominal Molecular Weight Cut-Off (NMWCO) of between 1-100,000.

As is known to those skilled in the art, NMWCO, or Molecular weight cut-off (MWCO), is a method of characterization used in filtration to describe pore size distribution and retention capabilities of membranes. It is defined as the lowest molecular weight (in Daltons) at which greater than 90% of a solute with a known molecular weight is retained by the membrane. As will be appreciated by those skilled in the art, the exact filter cut off will vary according to the species origin of the collagen being extracted (e.g. mammalian versus cnidaria) and so can be tailored accordingly. More preferably still, the first filter membrane has a NMWCO of 10,000-60,000. Most ideally, the first filter membrane has a NMWCO selected from 10,000 or 50,000.

In the above method, in particular step a), the original collagen containing sample is treated with alkaline or basic solution to allow cellular matter and other non-collagenous material to be destroyed and, in particular, the hydrolysis of fats and proteins which can then be removed through the membrane filtration system. As will be appreciated by those skilled in the art, an alkaline or basic solution is any solution whose pH lies between 7 to 14 and is well known it the art such as, but not limited to, any hydroxide solutions for example ammonium hydroxide, sodium hydroxide, potassium hydroxide, magnesium hydroxide or the like. Preferably, said alkali solution is sodium hydroxide.

In the above method, in a preferred embodiment, and in particular in step a), said collagen is provided in an alkaline/basic solution to allow cellular matter and other non-collagenous material to be destroyed, preferably at a sample/solution ratio of about 1:1 (w/v) to about 1:100 (w/v) and preferably at a sample/solution ratio of about 1:10 (w/v). Most preferably, the extraction is undertaken by circulation in a closed system, e.g. in a loop such as a circulation loop as illustrated in FIG. 3 for several days up to and including 3 days.

Preferably, in step b), the extraction is filtered using at least one 50,000 NMWCO hollow fibre membrane. Most preferably the extraction is filtered by circulation in a closed system, e.g. in a loop such as a circulation loop as illustrated in FIG. 4 to decrease the pH by filtering the basic/alkaline solution. Ideally, the extraction is filtered until a pH<8 is achieved and a first filter retentate is obtained.

As will be appreciated by those skilled in the art, due to the process of filtering there may be a gradual loss of solution volume and as such in a preferred embodiment of the method, in particular in step b) the first filter retentate is supplemented, before during or after filtering, with deionised water to maintain the original volume or the volume required for the execution of the subsequent method steps, so as to achieve optimum desired flow rate, recirculation volumes and the like according to the filter separation system.

Preferably, in step c), the first filter retentate is adjusted to make a solution having an essentially acidic pH of less than 7, preferably less than 5, and ideally less than 3. As will be appreciated by those skilled in the art, this can be achieved by supplementing with acidic solutions known in the art such as, but not limited to, acetic acid. Most preferably, the resultant acidified first filter retentate is then circulated in a closed system, e.g. in a loop such as a circulation loop as illustrated in FIG. 5 for several days at least up to and including 3 days, more preferably at least up to and including 7 days. As will be appreciated by those skilled in the art, this step facilitates the digestion of intramolecular bonds of the collagen fibrils and leads to partial cleavage of the telopeptide regions and thus partially solubilising the collagen.

Preferably, in step d), the first filter retentate is filtered to remove the acid, ideally until a pH of greater than 6 is achieved, and this preferably comprises the use of at least one 50,000 NMWCO hollow fibre membrane to obtain a second filter retentate. Ideally, this is undertaken in a circulation loop such as a circulation loop as illustrated in FIG. 4.

As will be appreciated by those skilled in the art, due to the process of filtration there may be a gradual loss of solute volume and where this occurs, in a preferred embodiment of step d), the second filter retentate is supplemented with deionised water preferably to maintain the original volume or the volume required for the execution of the subsequent method steps, so as to achieve an optimum desired flow rate, recirculation volumes and the like according to the filter separation system.

In yet a further preferred method of the invention, steps c)-d) are repeated at least once to improve yield and purity.

In a yet a further preferred method of the invention still, steps c)-d) are performed in a closed circulatory system that either runs constantly or runs constantly during the performance of the said specified steps.

In yet a further preferred embodiment of the invention said filtering involves the process of dialysis.

Those skilled in the art will appreciate that steps a-d may be omitted when using an acid soluble source of collagen. Accordingly in this embodiment the method simply involves the following steps:

e) adjusting the pH of the second filter retentate so that it is acidic thereby solubilising the collagen bound by same;

f) filtering the second filter retentate using at least one second filter membrane to produce a first filtrate comprising single alpha chain collagen; and g) optionally, filtering the first filtrate using said at least one first filter membrane to produce a second retentate comprising single alpha chain collagen.

Preferably, in step e), the second filter retentate is adjusted to make a solution having an essentially acidic pH of less than 7, preferably less than 5, and ideally less than 3. As will be appreciated by those skilled in the art, this can be achieved by supplementing with acidic solutions known in the field such as, but not limited to, acetic acid. Most preferably, the resultant acidified second filter retentate is then circulated in a closed system, e.g. in a loop such as circulation loop as illustrated in FIG. 3. As will be appreciated by those skilled in the art, this further acidification step leads to further cleavage of the intramolecular bonds of the collagen and full solubilisation of any collagen fibres.

Preferably, in step f), the second filter retentate is filtered through at least one second filter membrane to obtain a purified first filtrate. More preferably, the second filter retentate is filtered until a pH of less than 8 is obtained. Even yet more preferably, the second filter membrane is a microporous membrane. More preferably the second filter membrane comprises a pore size in the range of 0.05 to 2 μm, including every 0.01 μm integer therebetween. Yet more preferably the second filter membrane comprises a pore size of in the range of 0.1 to 1 μm, including every 0.01 μm integer therebetween, is used. Most ideally, a pore size of about 0.2 to 0.5 μm is used. Ideally the solution is circulated in a circulation loop such as a circulation loop as illustrated in FIG. 7.

As will be appreciated by those skilled in the art, due to the process of filtration there may be a gradual loss of solute volume and where this occurs, in a preferred embodiment of step f), the second filter retentate is supplemented with 0.5 M acetic acid (this can be 0.0 M-1 M as above) preferably to maintain the original volume or a total volume of at least 20% of reactor capacity to increase filtrate yield.

Preferably, in step g), the first filtrate is retained with said at least one first filter, preferably until a pH of less than 8 is achieved. Most preferably at least one 50,000 NMWCO hollow fibre membrane, to concentrate the solution to greater than 0.1 mg/ml but preferably 3-10 mg/ml and most preferably 6 mg/ml.

In a preferred embodiment of the invention, said collagen is of Mammalian or Cnidarian origin, such as ungulate or bovine/fish or jellyfish origin.

In yet a further preferred embodiment, said collagen is any type of collagen known to those skilled in the art such as, but not limited to, Type I, II, Ill, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, or XXIX. More preferably, said collagen is a fibril forming collagen selected from the group comprising: Type I, II, Ill, V, XI, XXIV, XXVI, XXVII or XXVIII. Most preferably, said collagen is selected from the group comprising: Type I, II, Ill, V, XXIV or XXVI.

According to a further aspect of the invention there is provided an isolated or purified product comprising or consisting of single alpha chain collagens (SAC), typically but not exclusively, obtained using one of the afore methods.

In a preferred embodiment, said product has at least 50% SACCs content per total collagen protein content, more ideally at least 75% SACCs content per total collagen protein content, or yet more ideally at least 85% SACCs content, or most ideally, 85%, 86%, 87%, 88%, 89%, 90%, 91%, 92%, 93%, 94%, 95%, 96%, 97%, 98%, 99% or 100% SACCs content per total collagen protein content. Preferably, said product does not comprise beta and/or gamma collagen i.e. double or triple helical chains, respectively.

In yet a further preferred embodiment, said SACCs are characterised by a molecular weight of about 50-150 kDa. More ideally, said SACCs are characterised by a molecular weight of about 80-120 kDa and most ideally about 90-110 kDa.

In yet a further preferred embodiment still, said single alpha chain (SACC) collagen comprises approximately 1000-3500 amino acids, yet more preferably it comprises between 1000-1500 amino acids. As is known by those skilled in the art, different collagen family members have varying amino acid lengths for both alpha1 and alpha2 chains, for example collagen I has chain lengths of 1464 and 1366 amino acids for alpha1 and alpha2, respectively, whereas collagen XXVI has an alpha1 chain length of 3051 amino acids (table 2). Accordingly, the length of the SACC will be determined by the nature of the starting collagen material as will be appreciated by those skilled in the art.

Yet more preferably still, said SACCs comprise N-terminal and/or C-terminal ends that exist in non-helical, or unwound, form, also known for the selective re-assembly of the single alpha chain structures into a double or triple helix and so provides for the potential for the production of double or triple helices from isolated SACCs, having regard to reaction conditions. This includes, for example, PBS, Media or other buffered salt solution at conditions matching physiological pH and salt content, at temperatures from 4-40° C.

As will be appreciated by those skilled in the art, isolation of said product, or SACCs, is characterised by having little or no triple helix present i.e. the single alpha chain collagens have not undergone association, with other single alpha chain collagens, to form a triple helix but rather exists wholly or substantially in a single alpha chain form. Triple helix formation/presence can be tested by numerous means known in the art such as, but not limited to, FTIR spectroscopy wherein SACCs are identified by a reduction of amide I absorbance at wavelength 1638 cm-1 compared to triple helix collagen.

More ideally still, the product of the inventive method is suspended in a solution suitable for the purpose of electrospinning. SACCs dissolve in benign solvents (acetic acid) as well as physiological buffers such as PBS, media etc. Indeed, it has been found that SACCs are extremely soluble in benign solvents such that concentrations of up to 98% w/v SACCs have been achieved. In contrast, conventional acid solubilised collagen is, as the name would suggest, poorly soluble in benign solutions and even then, at best, only soluble at concentrations typically (up to) around 10 w/v, wherein above that amount precipitation/suspension readily occurs. Further, the poor solubility of acid soluble collagen (ASC) also means that electrospinning at higher concentrations of ASC is not possible. Without wishing to be bound by theory, it is thought that the increased solubility of SACCs is owing to the fact that the isolated SACCs lack helical forms of collagen (e.g. beta and or gamma) and also possesses increased free hydrogen bonds. Accordingly, there is provided a benign buffer in which SACCs are dissolved. Advantageously, this solubility is important for applications in tissue engineering/medical devices etc. as the currently used HFP denatures the protein and causes immunological damage to tissues and patients.

Therefore, in yet a further preferred embodiment, said product comprises SACCs that have not been denatured and are dissolved in a benign solution such as but not limited to, physiological buffers, weak solvents, or water. In contrast, collagens isolated by other means, and not of SACCs form, can only be dissolved in such benign solutions following harsh denaturing protocols. In a preferred embodiment, said solution comprises SACCs at a concentration of at least 50% w/v, ideally at least 75% or yet more ideally at least 85% w/v, or most ideally, 85%, 86%, 87%, 88%, 89%, 90%, 91%, 92%, 93%, 94%, 95%, 96%, 97%, 98%, 99% or 100%.

According to a further aspect of the invention there is provided isolated single alpha chain collagens (SACCs) in aqueous solution wherein each SACC is a single chain polypeptide existing as an alpha helix and having a molecular weight of approximately 100 kDa and a repeating sub structure of Glycine-X-Y (where X can be any amino acid, and Y is proline or hydroxyproline).

In a preferred embodiment of this aspect of the invention said isolated SACCs do not include beta or gamma collagen, and most ideally, do not include beta and gamma collagen.

In a preferred embodiment of the invention, said collagen is of Mammalian or Cnidarian origin, such as ungulate or bovine/fish or jellyfish origin.

In yet a further preferred embodiment, said collagen is any type of collagen known to those skilled in the art such as, but not limited to, Type I, II, Ill, IV, V, VI, VII, VIII, IX, X, XI, XII, XIII, XIV, XV, XVI, XVII, XVIII, XIX, XX, XXI, XXII, XXIII, XXIV, XXV, XXVI, XXVII, XXVIII, or XXIX. More preferably, said collagen is a fibril forming collagen selected from the group comprising: Type I, II, Ill, V, XI, XXIV, XXVI, XXVII or XXVIII. Most preferably, said collagen is selected from the group comprising: Type I, II, Ill, V, XXIV or XXVI.

In yet a further preferred embodiment still, said single alpha chain (SACC) collagen comprises approximately 1000-3500 amino acids, yet more preferably comprises between 1000-1500 amino acids.

In a preferred embodiment, said isolated SACCs have at least 50% SAC per total collagen content, more ideally at least 75% SACCs per total collagen content, or yet more ideally at least 85% SACCs per total collagen content, or most ideally, 85%, 86%, 87%, 88%, 89%, 90%, 91%, 92%, 93%, 94%, 95%, 96%, 97%, 98%, 99% or 100% SACCs per total collagen content.

In yet a further preferred embodiment, said SACCs are characterised by a molecular weight of about 50-150 kDa. More ideally, said SACCs are characterised by a molecular weight of about 80-120 kDa and most ideally about 90-110 kDa.

Yet more preferably still, said SACCs comprise N-terminal and/or C-terminal ends that exist in non-helical, or unwound, form, also known for selective re-assembly of the single alpha chain structures into a double or triple helix and so provides for the potential to produce double or triple helices from isolated SACCs, having regard to reaction conditions. This includes, for example, PBS, Media or other buffered salt solution at conditions matching physiological pH and salt content, at temperatures from 4-40° C.

Using our methods the isolation of SACCs occurs with little or no triple helix formation. Therefore, according to a further preferred embodiment said SACCs are characterised by little or no or reduced gamma collagen or triple helix formation. The presence of triple helices or triple helix formation can be tested by numerous means as known in the art such as, but not limited to, FTIR spectroscopy wherein single alpha chain collagen is identified by reduction of amide I absorbance at wavelength 1638 cm-1 compared to triple helix collagen.

In a preferred embodiment, said solution comprises SACCs at a concentration of at least 20% w/v, ideally at least 50% or yet more ideally at least 85% w/v, or most ideally, 85%, 86%, 87%, 88%, 89%, 90%, 91%, 92%, 93%, 94%, 95%, 96%, 97%, 98%, 99% or 100%.

According to a further aspect of the invention there is provided the use of said isolated SACCs for electrospinning.

Accordingly, there is also provided a suspension of said isolated SACCs wherein said suspension comprises a solution suitable for electrospinning. Said isolated SACCs electrospin in benign solvents (acetic acid) as well as physiological buffers such as PBS, media etc. This is an important and advantageous feature for tissue engineering applications and medical devices as the HFP used currently in electrospinning denatures the protein and causes immunological damage to tissues and patients. As discussed, conventional extracts of collagen are poorly soluble in such benign aqueous solutions and thus cannot be electrospun in same and, moreover, the presence of gamma collagen in such extracts and the lack of non-helical ends limits their utility.

Therefore, according to a further aspect of the invention, there is provided an electrospinning solution comprising the isolated SACCs as herein described.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

BRIEF DESCRIPTION OF THE DRAWINGS

The invention will now be described, by way of example only, with reference to the following figures and tables wherein:

FIG. 1. A basic electrospinning set up using a syringe pump and high voltage power supply connected with a grounded collector plate;

FIG. 2. Chart of extraction stages which contain critical points necessary to avoid solubility issues with collagen extracts;

FIG. 16A: SDS PAGE of SACCs extracted from *Rhizostomas pulmo* showing collagen bands present in solution. Lanes 1&2: Benchmark High Molecular Weight Protein Ladder. Lanes 3-4: Collagen Solution Containing α1, α2 Collagen Chains with high molecular weight β & γ chains removed. FIG. 16B: SDS PAGE of electrospun SACCs extracted from *Rhizostomas pulmo* redissolved in 0.5 M AcOH post electrospinning showing collagen bands present in solution. Lanes 1&2: Benchmark High Molecular Weight Protein Ladder. Lanes 3-4: Collagen Solution Containing α1, α2 Collagen Chains without high molecular weight β & γ chains;

FIGS. 18A-18B. FIG. 18A: SEM Micrograph of needle electrospun jellyfish collagen fibres using a Hitachi S4800 FEG-SEM at an acceleration voltage of 10 kV, emission current of 9 μA and magnification of 1500×. Solution composition was 25% collagen (w/v) in a 90% AcOH solution (v/v). Fibre Diameter is shown to be 646 nm ±121 nm. Scale Bar=10 μm. FIG. 18B: Frequency of Range of SACCs Nanofibres from Jellyfish Sources from 0.3 μm to 1.1 μm. with a fibre diameter of 646 nm±121 nm;

FIG. 21A: SEM Micrograph of needle electrospun bovine collagen fibres at an acceleration voltage of 10 kV, emission current of 9 μA and magnification of 1500×. Solution composition was 35% collagen (w/v) in a 90% AcOH solution (v/v). Fibre Diameter is shown to be 84 nm ±27 nm. Scale Bar=1000 nm.

FIG. 21B: Frequency of Range of SACCs Nanofibres from Bovine Sources; as above range is from 40 nm to 270 nm with a fibre diameter of 84 nm±27 nm;

FIG. 22A: SEM Micrograph of needle-less electrospun bovine collagen fibres at an acceleration voltage of 2 kV and magnification of 1800×. Solution composition was 25% collagen (w/v) in a 90% AcOH solution (v/v). Fibre Diameter is shown to be 1128 nm ±406 nm. Scale Bar=30 μm. FIG. 22B: Frequency of Range of SACCs Nanofibres from Jellyfish Sources Produced with Needle-less Electrospinning Techniques, range is from 0.2 μm to 2.4 μm with an average fibre diameter of 1128 nm±406 nm;

FIG. 23A: SACCs electrospun from PBS solution with an acceleration voltage of 5 kV and magnification of 10,000×. Solution composition was 20% collagen (w/v) in a 1×PBS solution. Fibre diameter is shown to be 105 nm ±28 nm. Scale Bar=5 μm. FIG. 23B: Frequency of range of SACCs nanofibres electrospun from a solution of 20% collagen in 1×PBS;

FIG. 32B: Single alpha chain collagen (SACC). ASC clearly comprises a triple helical structure, whereas SACC is composed of a single helical alpha chain. Moreover, unlike ASC wherein intramolecular bonding within in the triple helical structure leads to less free unoccupied hydrogen bonds, SACC has a much greater free hydrogen bond content per chain leading to improved solubility in benign solvents up to 99% by weight;

FIG. 33A: SACC comprises single alpha 1 and alpha 2 chains but is free from contamination with beta and gamma chains. FIG. 33B: ASC comprises a mixture of alpha 1 and alpha 2 chains, but also high molecular weight beta and gamma chains.

FIG. 33C: ASC when comprising 60% alpha chain composition still has substantial beta and gamma chain contamination that limits downstream utility;

FIG. 35A: 10% ASC in 100% hexafluoropropanol (HFP) following 48 h solubilisation; FIG. 35B: 10% ASC in 90% acetic acid; FIG. 35C: 10 ASC in 45% Acetic Acid; FIG. 35D: 25% jellyfish SACC in 90% Acetic Acid; FIG. 35E: 20% bovine SACC in 1× Phosphate buffered saline. Acid Soluble Collagen (ASC) does not electrospin without the use of HFP or other fluorinated solvent (i.e. TFE) [A-C], and non-denatured (Gamma containing) ASC electrospun with Acetic Acid (AcOH) produces micro/nano spheres (B-C). In contrast, Single alpha chain collagen (SACC) electrospins without the use of HFP or other fluorinated solvents but instead can be achieved using benign solvents such as acetic acid and physiological buffered (PBS) solutions.

Figure 3:
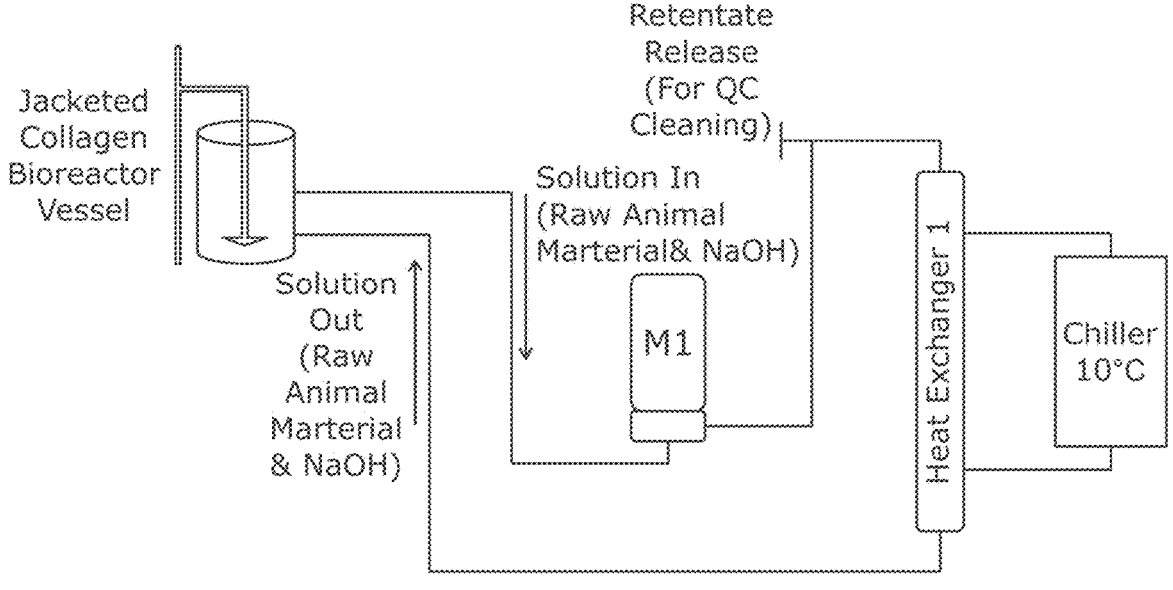
FIG. 3. Loop 1 in collagen extraction, material is circulated to control temperature at 10° C. or lower.

Table 1. Peak Picking of FTIR absorption values for analysis of corresponding vibrations in secondary structure;

Table 2. Typical amino acid chain lengths of alpha1 and/or alpha2 chains of a selection of different collagen molecules

METHODS & MATERIALS

Collagen Extraction Method
Traditional Acid Solubilisation—Freeze Dried Jellyfish Material The freeze-dried Jellyfish was thawed at 4° C. overnight. This was then cut into pieces of 0.5 cm$^2$ and washed with distilled water to remove large impurities and rehydrate the specimen. The samples were then treated with 0.1 M NaOH (1 M Stock, Fisher, UK) at a sample/solution ratio of 1:10 (w/v). This was then stirred using a magnetic stirrer for 2 days at 4° C. The solution was then filtered through cheese-cloth, followed by glass wool to remove any insoluble material. The solution was then poured into dialysis tubing and dialyzed against 5 L of Dialysis Buffer at 4° C. which was changed daily for 3 days. The collagen then began precipitating out of solution and appeared as a white solid. The collagen containing solution was then centrifuged at 10,000 rpm/16,000 g for 10 minutes at 4° C. This was then suspended in 500 ml 0.15 M acetic acid for 48 h at 4° C. to purify the collagen. 25 g of solid NaCl was then added to give a concentration of 5% and overnight incubation at 4° C. dissolved the salt, causing the displacement and precipitation of the collagen. The centrifugation through to salting out was repeated twice to further purify collagen, followed by a final centrifugation at 10,000 rpm for 10 minutes at 4° C. The final pellet was dissolved in 500 mL 4° C. 0.15 M Acetic Acid and dialyzed against Dialysis Buffer for 5 consecutive days at 4° C. to remove all traces of NaCl, ensuring the Dialysis Buffer was changed daily. The solution was then centrifuged at 10,000 rpm/16,000 g for 10 minutes at 4° C. and the pellet suspended in 70% Ethanol (Absolute Stock, Fisher, UK) to sterilize the collagen. This solution was stirred at 4° C. for 48 hr, and collected by centrifugation at 10,000 rpm for 10 min at 4° C. The collagen solution was then transferred in a laminar flow hood to sterile, pre-weighed 50 ml tubes. This was then frozen at −80° C.

overnight and lyophilised the following day using a freeze drier. The tubes were weighed and compared to their empty weight using a scale and the weight of the collagen determined. 0.15 M Acetic Acid was added to give a final concentration of collagen of 3 mg/ml.

Traditional Acid Solubilisation—Whole Jellyfish Material

Separated jellyfish bells or tentacles were thawed overnight at 4° C. and drained of any residual liquid. Weight was recorded for comparison to catch weight and final yield calculations. The samples were washed with distilled water to remove any foreign bodies until the bell or tentacles were almost clear. These were then blended roughly to produce a slush consistency of material ready for processing. The samples were then treated with 0.1 M NaOH (1 M Stock, Fisher, UK) at a sample/solution ratio of 1:10 (w/v). This was then stirred using a magnetic stirrer for 2 days at 4° C. The solution was then filtered through cheesecloth, followed by glass wool to remove any insoluble material. The solution was then poured into dialysis tubing and dialyzed against 5 L of Dialysis Buffer at 4° C. which was changed daily for 3 days. The collagen then began precipitating out of solution and appeared as a white solid. The collagen containing solution was then centrifuged at 10,000 rpm/16,000 g for 10 minutes at 4° C. using a centrifuge. This was then suspended in 500 ml 0.15 M acetic acid for 48 h at 4° C. to purify the collagen. 25 g of solid NaCl was then added to give a concentration of 5% and overnight incubation at 4° C. dissolved the salt, causing the displacement and precipitation of the collagen. The centrifugation, through to salting out was repeated twice to further purify collagen, followed by a final centrifugation at 10,000 rpm for 10 minutes at 4° C. The final pellet was dissolved in 500 mL 4° C. 0.15 M Acetic Acid and dialyzed against Dialysis Buffer for 5 consecutive days at 4° C. to remove all traces of NaCl, ensuring the Dialysis Buffer was changed daily. The solution was then centrifuged at 10,000 rpm/16,000 g for 10 minutes at 4° C. and the pellet suspended in 70% Ethanol (Absolute Stock, Fisher, UK) to sterilize the collagen. This solution was stirred at 4° C. for 48 hr, and collected by centrifugation at 10,000 rpm for 10 min at 4° C. The collagen solution was then transferred in a laminar flow hood to sterile, pre-weighed 50 ml tubes. This was then frozen at −80° C. overnight and lyophilised the following day using a freeze drier. The tubes were weighed and compared to their empty weight using a scale and the weight of the collagen determined. 0.15 M Acetic Acid was added to give a final concentration of collagen of 3 mg/ml.

Membrane Extraction—Jellyfish

The frozen jellyfish material which had been earlier separated into either tentacles or bells were thawed at 4° C. overnight and thoroughly washed with RO water, until no foreign bodies were present and the material was almost clear. This material was blended thoroughly until no chunks of material present were larger than 1 mm in diameter. This was then pumped into the bioreactor vessel by use of a peristaltic pump and autoclaved tubing. The samples were then treated with 0.1 M NaOH (1 M Stock, Fisher, UK) at a sample/solution ratio of 1:10 (w/v). The solution was run under circulation loop 1 as demonstrated in FIG. 3 for 3 days to allow cellular matter and other non-collagenous material to be destroyed and, in particular, the hydrolysis of fats and proteins which can allow for their removal through the membrane system.

Figure 4:
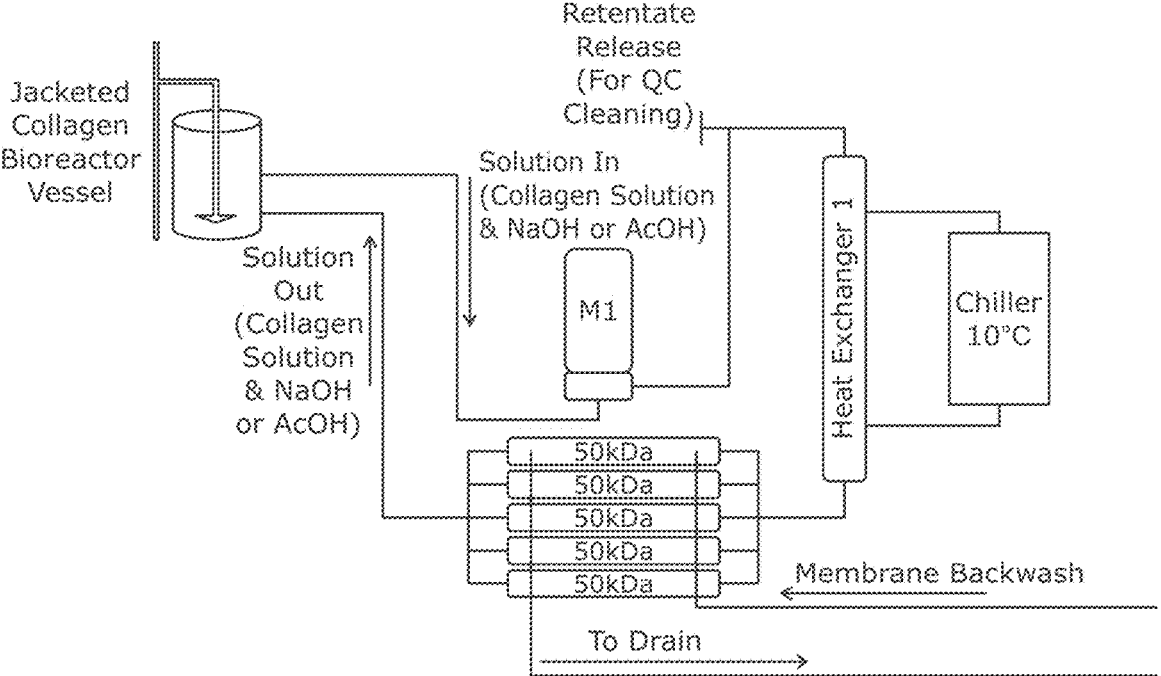
FIG. 4. Loop 2 in collagen extraction; material is circulated to control temperature and is retained by 1-100,000 NMWCO (10 kDa representative) hollow fibre membranes to remove NaOH and non-collagenous material from system.
Figures 5, 6:
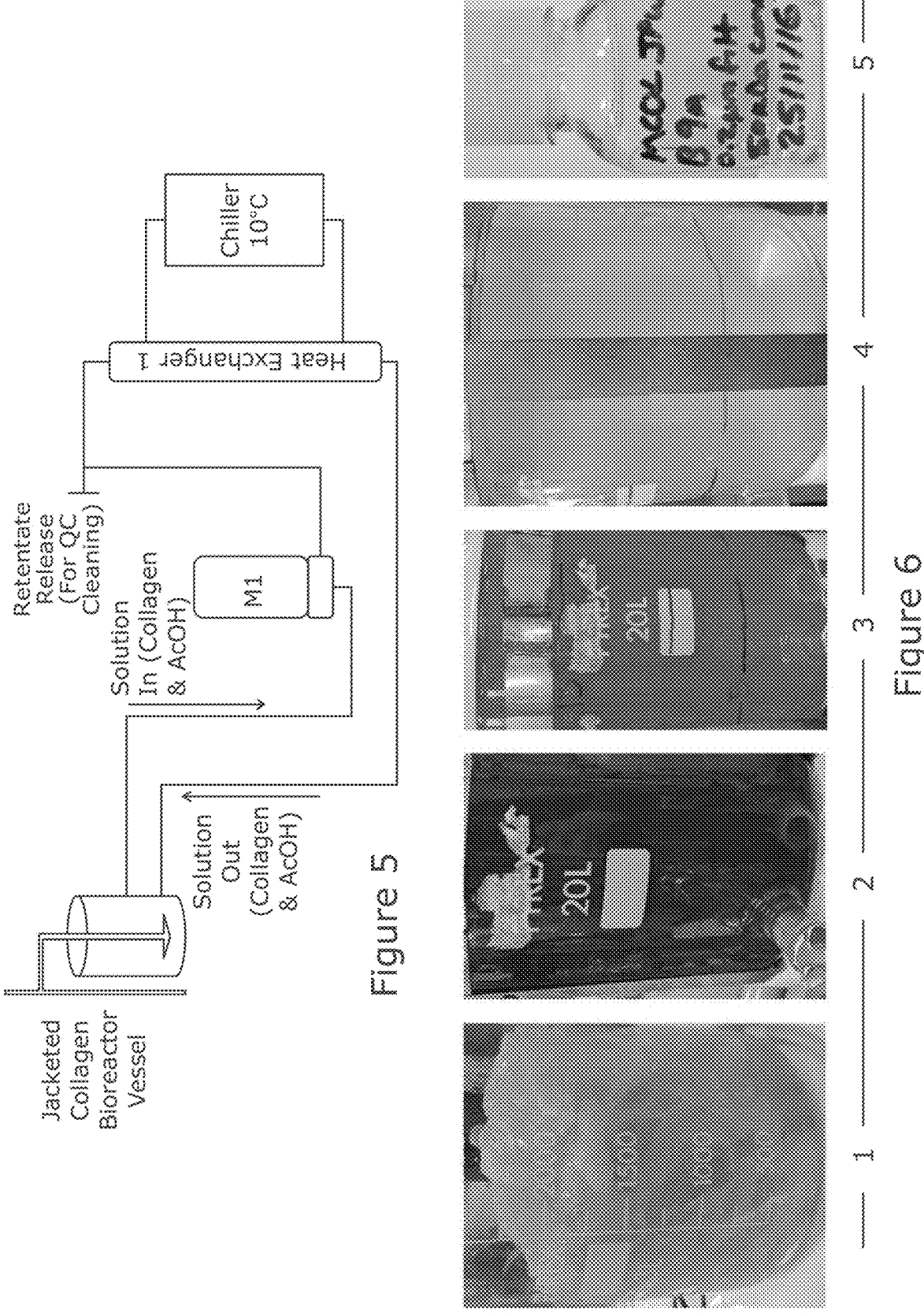
FIG. 5. Loop 3 collagen circulation through heat exchanger to maintain temperature at or below 10° C. while acid solubilisation occurs.
FIG. 6. Progress of extraction—1: Raw Starting Material. 2: NaOH Treatment. 3: Dialysis & AcOH Treatment. 4: Second Dialysis and AcOH Treatment. 5: 0.2 μm filtered, 50 kDa concentrated SACCs.

The solution was then dialysed using loop 2 as shown in FIG. 4 to remove NaOH from solution using a 10,000 NMWCO hollow fibre membrane. The reduction in volume is then replaced with Deionised water to maintain total volume of 20% reactor capacity. The solution was filtered until a pH<8 was obtained. The remaining capacity of the bioreactor was then filled to capacity with the appropriate volume of acid and RO water to make a final concentration of 0.5 M acetic acid. This was then cycled under loop 3 as shown in FIG. 5 for 3 days to allow the collagen to interact and undergo partial cleavage of the telomeric regions.

Following this, the solution was again dialysed to remove the acid using loop 2 as shown in FIG. 4 using a 50,000 NMWCO hollow fibre membrane. The reduction in volume was replaced with water to maintain a total volume of 20% of reactor capacity and the solution was filtered until a pH >6.5 was obtained and subsequently replenished to 0.5 M AcOH at 100 L capacity to increase yield. This was repeated 3 times in total before the volume of solution was reduced as much as possible to leave a highly concentrated mixture ready to be dried. Once dialysed and concentrated, samples of the solution were lyophilised to determine dry weight of the collagen.

Membrane Extraction—Bovine Insoluble Collagen

The bovine insoluble collagen was purchased from Sigma (UK) and stored at 4° C. until use. This insoluble material was then hydrated in RO water and blended thoroughly until no chunks of material present were larger than 1 mm in diameter. This was then pumped into the bioreactor vessel by use of a peristaltic pump and autoclaved tubing. The samples were then treated with 0.1 M NaOH (1 M Stock, Fisher, UK) at a sample/solution ratio of 1:10 (w/v). The solution was run under circulation loop 1 as demonstrated in FIG. 3 for 3 days to ensure non-collagenous material was destroyed as initial collagen purity was indicated at ~60%; this allowed for removal through the membrane system. The solution was then dialysed using loop 2 as shown in FIG. 4 to remove NaOH from solution using a 10 NMWCO membrane. The reduction in volume is then replaced with DI to maintain total volume of 20% reactor capacity. The remaining capacity of the bioreactor was then filled to capacity with the appropriate volume of acid and RO water to make a final concentration of 0.5 M acetic acid. This was then cycled under loop 3 as shown in FIG. 5 for 3 days to allow the collagen to interact and undergo partial cleavage of the telomeric regions.

Following this, the solution was again dialysed, instead to remove the acid as in loop 2, and subsequently replenished to 0.5 M AcOH at 100 L capacity to increase yield. This was repeated 3 times in total before the volume of solution was reduced as much as possible to leave a highly concentrated mixture ready to be dried. Once dialysed and concentrated, samples of the solution were lyophilised to determine dry weight of the collagen. The overall process can be seen in FIG. 6.

Single Alpha Chain Collagens (SACCs) Isolation—all Species

Figure 7:
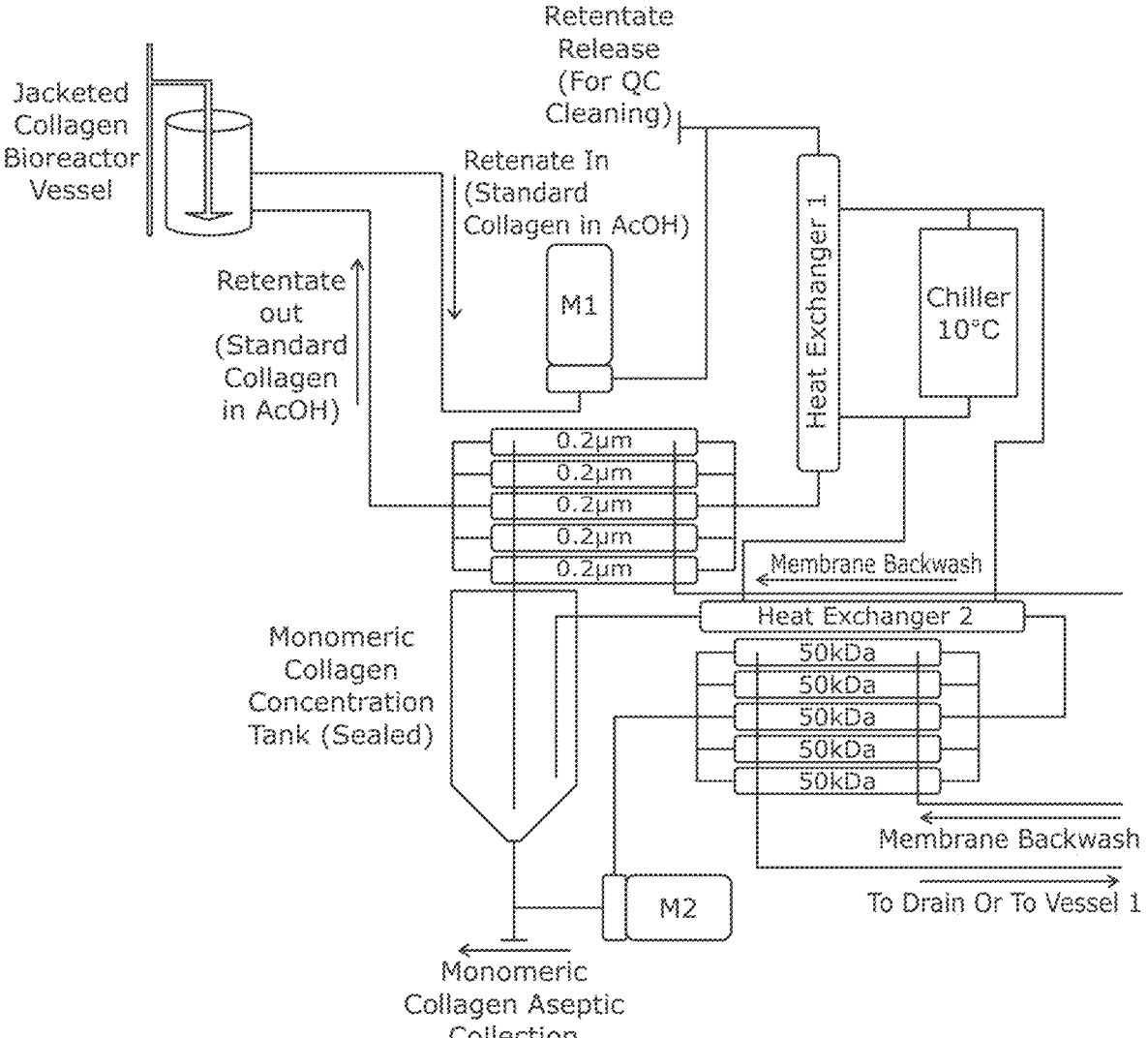
FIG. 7. Cycle of collagen treatment through crossflow filtration system to produce SACCs solutions.

The collagen produced using the extraction protocols above was diluted to 100 L at an AcOH concentration of 0.5 M in preparation for SACCs. These materials were allowed to fully disperse overnight at 4° C. while run under circulation loop 1 as shown in FIG. 3 then subjected to loop 4 as shown in FIG. 7 which comprised the inclusion of a 0.2 μm hollow fibre membrane. The retentate was recycled and kept at 100 L with input of fresh 0.5 M AcOH using peristaltic pump and autoclaved tubing. The permeate of the system was collected aseptically into a 20 L vessel which acted as a feed tank for loop 5 also shown in FIG. 7 which pumped the 0.2 μm permeate solution across a 50 NMWCO hollow fibre membrane to concentrate the solution and allow the removal of the ~40 kDa protein present in jellyfish collagen extracts seen in FIG. 16. The collagen solution was concentrated to <1 L and collected aseptically by pumping from the sealed container for bottling in a class II biological cabinet which was cleaned under standard cell culture practice. The subsequent material containing either pure α1 & α2 collagen fibres or a mixture alpha and β-collagen chains was stored at 4° C. for use in further characterisation or frozen at −80° C. overnight and lyophilised and stored as a dry sponge/powder. The retentate from the 0.2 μm filtration was concentrated to the minimum volume and stored for further characterisation.

Collagen Characterisation

SDS PAGE

SDS-PAGE analysis was carried out on samples before electrospinning to monitor for any changes to the presence or absence of particular chains of collagen alpha helix molecules. 7.5 μL Collagen (3 ng/mL) dissolved in Acetic acid at 4° C. was mixed with 2.5 μL NuPAGE® LDS Sample Buffer (4×) (Life Technologies, UK). This mixture was then heated at 70° C. in an incubator to reduce the collagen. Running buffer was prepared using 50 mL 20× NuPAGE® Tris-Acetate SDS Running Buffer added to 950 mL deionized water. NuPAGE® Tris Acetate Mini Gels were loaded into the holding clamp frame (Jencons, UK) and the running buffer added accordingly: 200 mL inner chamber, 600 mL outer chamber. The samples were then loaded alongside repeats of Benchmark™ Unstained Protein Ladder (Novex, UK) and the gel ran at 150V using a concord powerpack. Observed current ran from starting 45 mA to final 27 mA. After running, the gel was removed from the setup and placed into a tray for staining.

Staining (Coomassie)

The gel was stained using Colloidal Blue staining kit (Invitrogen) based on work described by (Neuhoff, Arold, Taube, & Ehrhardt, 1988). Briefly, the gel was initially stained using a mixture of Stainer A, composed of ammonium sulphate in a phosphoric acid solution, and Stainer B containing the Coomassie Brilliant Blue (CBB) G-250 Stain, with further addition of ultra-pure water and methanol. This mixture forms particles of colloidal dye which in combination with the methanol, shifts the equilibrium of the CBB G-250 stain from the colloidal form to a molecularly dispersed dye, allowing complete diffusion into the dye. This solution is left to shake for a minimum of 3 hours and is then decanted and replaced with ultra-pure water overnight to remove any dye not bound to the protein bands. The stained gels were then imaged and examined using ImageJ software.

Electrospinning

Needle Based Electrospinning

Purified Collagen Extract was produced in house for use in these experiments from Bovine and Rhizostoma pulmo jellyfish sources. Collagen was prepared by examination using SDS PAGE and freeze drying sufficient material for use. To compare the impact of the presence of high molecular weight collagen chains on the ability of collagen to electrospin, isolation of α1 & α2 chains from the β and γ chains was carried out. Crossflow filtration was utilised with a hollow fibre membrane of 0.2 μm nominal pore diameter. A 20 L solution of 10 mg/mi 'standard' collagen dissolved in 0.5 M acetic acid (AcOH) was passed through the hollow fibre in a loop system at 1.5 Bar, 200 L/h circulation. This allowed a weak solution of α1 & α2 single alpha chain collagens to be obtained, which was then concentrated to ~3 mg/ml by utilising a 50,000 NMWCO hollow fibre membrane. This Process is shown in FIG. 7. This was also examined using SDS PAGE analysis against the standard collagen extract, then lyophilised in preparation for electrospinning. To achieve adequate drying, samples were first aliquoted and frozen at −20° C. for 24 hours, and then transferred to −80° C. as Lyostat analysis of the collagen solutions showed an onset of collapse of ~32.5° C. (Carried out by Biopharma Technologies). The samples were transferred to the Scanvac CoolSafe™ freeze drier for drying. Once pressure was at 100 par, shelf temperature was measured at −30° C. and the primary drying stage of the process was carried out for 100 hours. Following this, shelf temperature was raised to +10° C. for 15 Hours for the secondary drying stage. Samples were then removed from the drier and weighed before being stored in sealed containers with silica pouches at 4° C. until use. A solution of 90% AcOH from Glacial in DI (v/v) was produced and chilled to 4° C. Following this, the dried collagen samples were weighed and added to an appropriate amount of AcOH to produce a collagen solution of between 10-50% (w/v). This was vortexed thoroughly until the collagen was fully dissolved and a consistent liquid was produced and was stored at 4° C. to prevent the collagen from denaturing.

Figure 17:
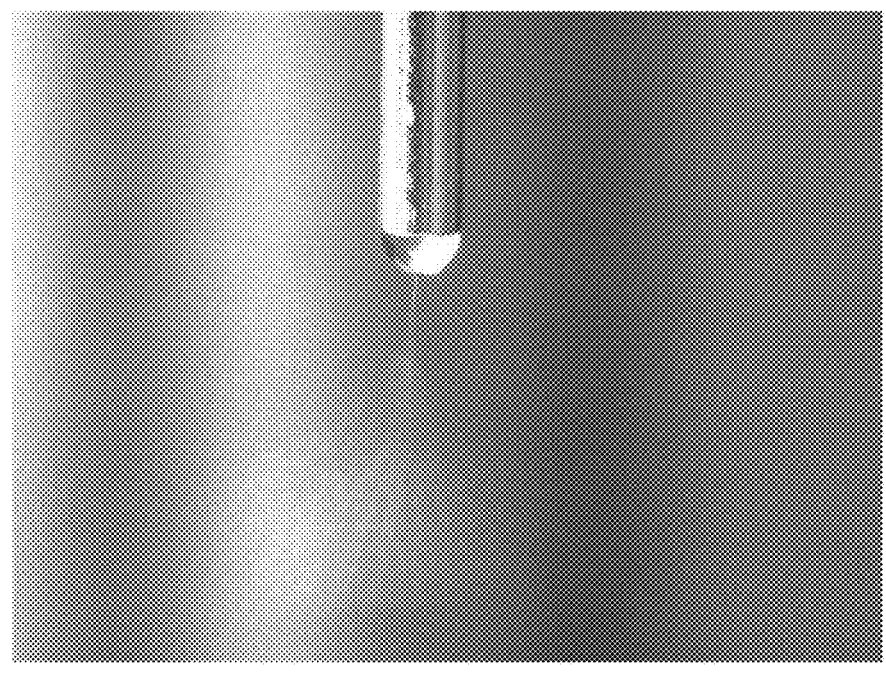
FIG. 17. Jellyfish SACCs solution being electrospun with constant droplet replenishment and a single taylor cone producing a jet of collagen solution which lands on the grounding target as collagen nanofibers.
Figure 19:
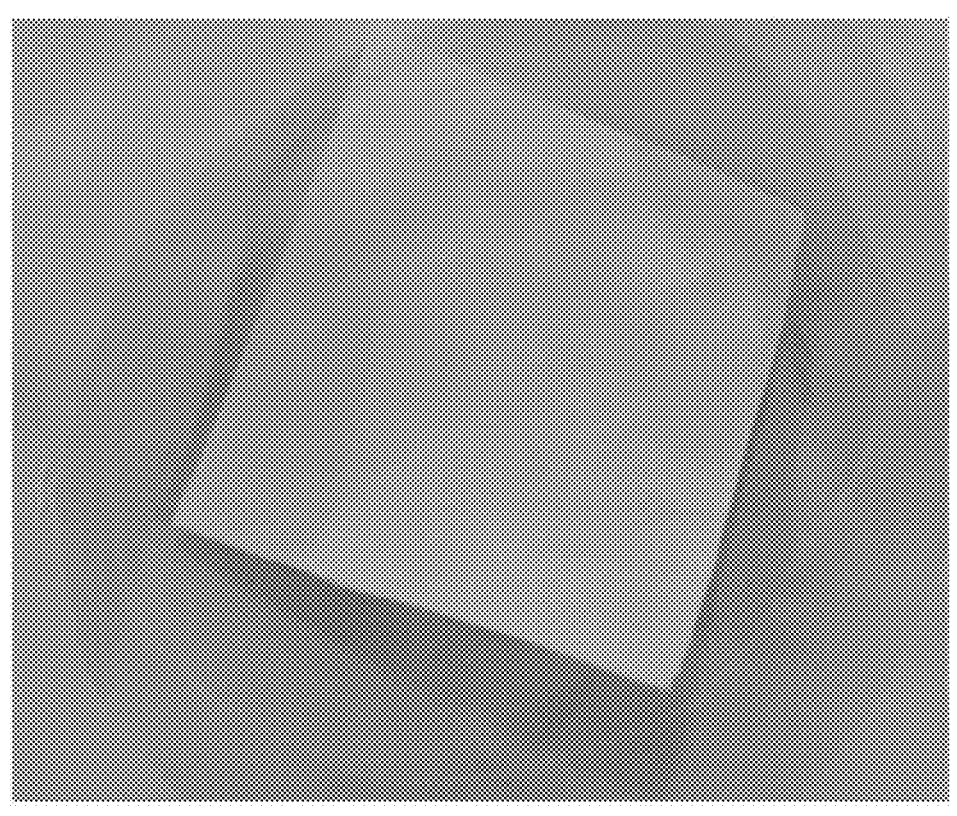
FIG. 19. Electrospun Mat of SACCs consisting of pure α1 & α2 collagen chains.

The electrospinning apparatus was set up using aluminium foil as the grounding target and was connected to ground. The syringe pump was set up to the correct diameter for a BD Plastipak® 10 ml needle and an 18 G blunt tipped needle was used. These were rinsed with DI, followed by a blank 90% AcOH solution prior to the solution being taken into the syringe and any air was cleared before loading onto the syringe pump. The syringe pump was set to use a flow rate of 0.35 mL per hour. The distance from needle tip to collector was 25 cm and a voltage of 18 kV was used. Voltage was applied when a droplet had formed at the tip of the needle and flow was maintained so volume of the droplet did not increase or reduce; an example of this setup is shown in FIG. 1. Taylor cone formation and electrospinning was observed using a camera and laser as shown in FIG. 17 and a 90% AcOH bath was placed in the electrospinning unit to prevent gelation of the droplet during periods of prolonged electrospinning. After electrospinning, the voltage was stopped and the equipment made safe, any remaining collagen was stored at 4° C. for characterisation. The mat produced was then sampled and coated in a 5 nm layer of chromium before being examined by scanning electron microscopy (SEM) using a Hitachi S4800 FEG-SEM at an acceleration voltage of 10 kV and emission current of 9 μA. Micrographs were taken with a magnification of 1500× for fibre diameter measurements, which were analysed using ImageJ software (Schneider, Rasband, & Eliceiri, 2012).

Needle-Less Electrospinning

For needle-less electrospinning, samples were freeze dried in the same manner and again dissolved at 25% concentration in a solution of 90% AcOH in DI. The solution was then placed in a bath and a mandrel with wires was submerged in the solution. The bath was inserted into the Nanospider NS Lab 200 System (Elmarco, Czech Republic) and a collection material placed over the grounding target. The Needle-less electrospinning process which has been previously described by (Burke et al., 2017); adapts the standard electrospinning approach to allow the formation several polymer jets simultaneously in order to allow for scalable fibre production. The process begins by applying a high voltage to a polymer bath which is continuously coating a 6 wire mandrel with droplets of polymer solution, which when exposed to the high voltage becomes elongated and Taylor cone formation occurs, forming multiple ejection points across the wire. The solution then undergoes rapid drying before being deposited on the collector. The material setup used a mandrel rotation speed at 10 revolutions per minute, a distance from mandrel tip to collector of 30 cm and a mandrel to collector voltage of 80 kV. Using these conditions, the current from mandrel to collector was observed to remain between 100 and 120 µA, signalling consistent fibre formation to be occurring. The process was carried out for 1 hour before being removed and samples taken for SEM imaging and characterisation as described above. Any remaining collagen solution was removed and stored at 4° C. for further solution testing, and the mat was sealed with silica packs to prevent excess moisture and kept at 4° C.

PBS Electrospinninq of Single Alpha Chain Collagens (SACCs)

SACCs which were lyophilised previously were removed from the fridge and dissolved at a concentration of 20% in a 1×PBS solution at 4° C. This was then mixed until fully dissolved and placed into a 5 mL syringe. The solution was electrospun at a distance of 12 cm and a voltage of 16 kV with a flow rate of 0.35 mL/hour. The resulting mat was taken for analysis by SEM, SDS PAGE and FTIR.

Crosslinking

Collagen nanofiber mats were crosslinked for use in applications where stability in water or media was required at temperatures above 30° C. This was required due to i) the increased surface area gained by electrospinning causing swelling and movement of the fibres, ii) the temperature stability of jellyfish collagen being too low for use in tissue scaffolds and 3D cell culture experiments and iii) for single alpha chain collagens' stability in hydrophilic solutions such as PBS. In this process, the crosslinker selected was 1-ethyl-3-(3-dimethyl aminopropyl) carbodiimide (EDC).

EDC Crosslinking

To crosslink the samples with EDC, a solution of 1% EDC in ethanol (w/v) was produced and samples were submerged in the crosslinking solution for a minimum of 4 hours while being clamped in place to prevent any swelling or shrinking deformation of the structure of the mat. Following this, the EDC solution was removed and the mats were soaked with pure ethanol for 24 hours, and then washed 3 times with DI before being placed in a desiccator to dry.

FTIR of Collagen

Collagen samples were examined using a Perkin Elmer FTIR/ATR device using a soft tip. For liquid samples 54 of solution was placed on the diamond stage and allowed to dry. The samples were then tested using a scan range from 4000-400 cm$^{-1}$. Once background correction was carried out, the data was normalised and was analysed using the Spectrum software and compared between samples to give a percentage similarity. This data was then exported and analysed for changes to secondary structure elements, as well as triple helix abundance.

Results

Collagen Extraction

Traditional Acid Solubilisation—Freeze Dried Jellyfish Material

Figure 8:
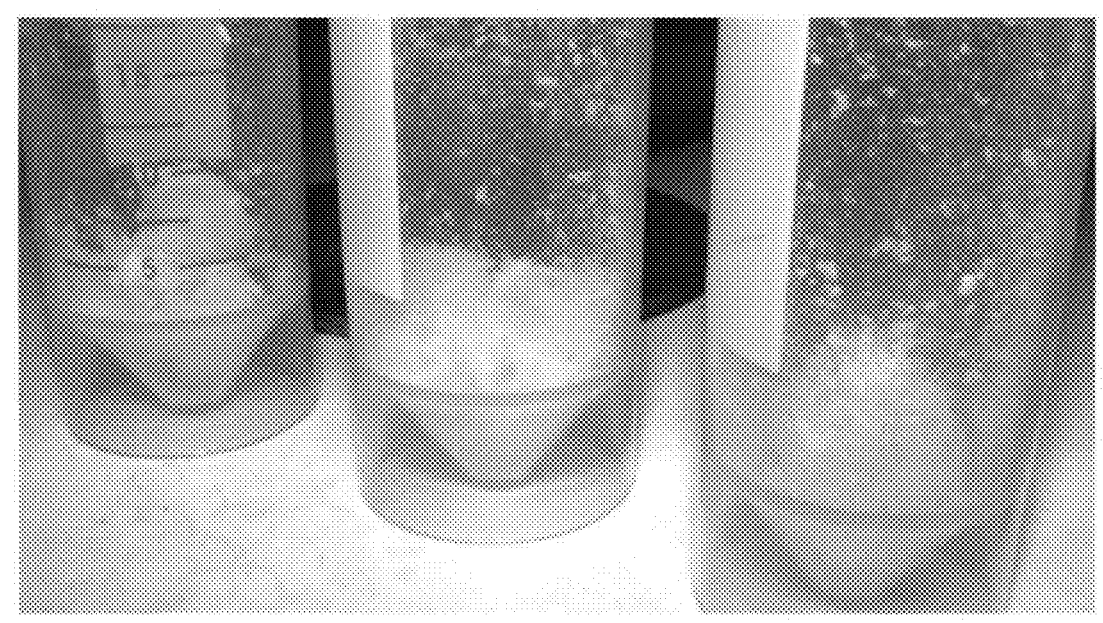
FIG. 8. Collagen powder obtained through traditional extraction on freeze dried jellyfish material.

The freeze dried material which was extracted using the centrifugation based method achieved a yield of 0.061% based on the original catch weight of the jellyfish, signifying that 1 kg of jellyfish would yield 0.61 g of collagen. This yield makes the extraction of collagen very expensive and time consuming, and the collagen produced had a low structural rigidity, making its use for tissue engineering scaffolds ineffective. The process involved a two-week extraction protocol which was limited in effectiveness by the need for centrifugation, limiting the extractability to around 400 mL per centrifugation cycle. A per person limit for this process is then described as 4 L total volume of solution, equating to 400 g of starting material, and just 0.24 g of collagen per run as seen in FIG. 8. Electrospinning typically requires a minimum of 1 mL of solution for a small scaffold to be produced, which based upon 10% collagen in the mixture would require 1 batch run of this process per 2 electrospun scaffolds and would require the use of HFP in order for the collagen to electrospin.

Traditional Acid Solubilisation—Whole Jellyfish Material

Figure 9:
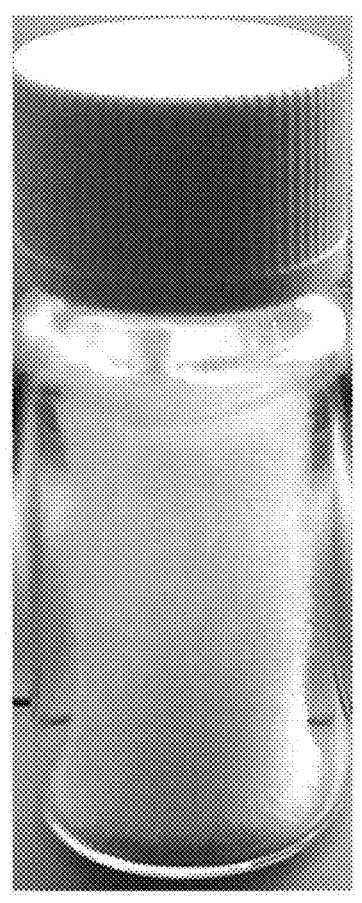
FIG. 9. Collagen sponge obtained through traditional extraction on hydrated jellyfish material.

The whole jellyfish material which was extracted using the centrifugation based method achieved a yield of 0.032% based on the original catch weight of the jellyfish, signifying that 1 kg of jellyfish would yield 0.32 g of collagen. This yield makes the extraction of collagen more time consuming, however the quality of the scaffold was slightly higher, retaining some sponge like appearance as seen in FIG. 9. The process involved the same two-week extraction protocol as above which was limited in effectiveness by the need for centrifugation, this means a per person limit for this process is just 0.13 g of collagen per run. This would require one batch run per electrospun scaffold produced and would still require the use of HFP to electrospin the collagen into a nano-fibrous scaffold.

Membrane Extraction—Jellyfish

Figure 10:
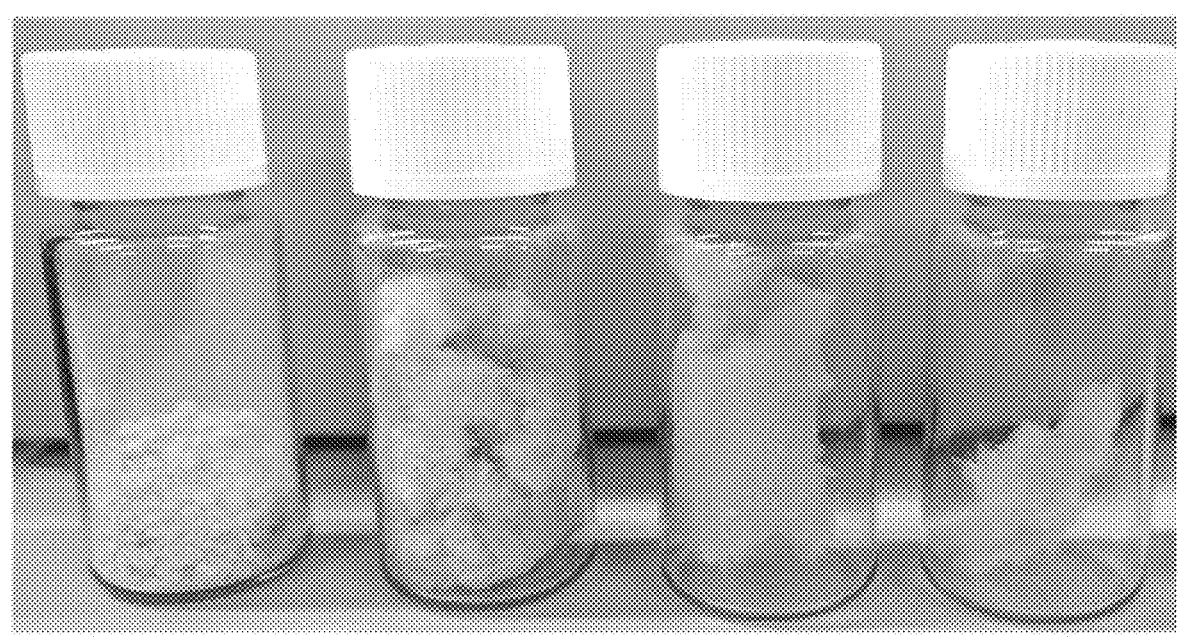
FIG. 10. (Left to Right) a) Spray Dried Collagen. b) Freeze Dried Collagen Sponge (12 mg/mL). c) Freeze Dried Collagen Sponge (6 mg/mL). d) Freeze Dried Collagen Sponge (3 mg/mL)
Figure 11:
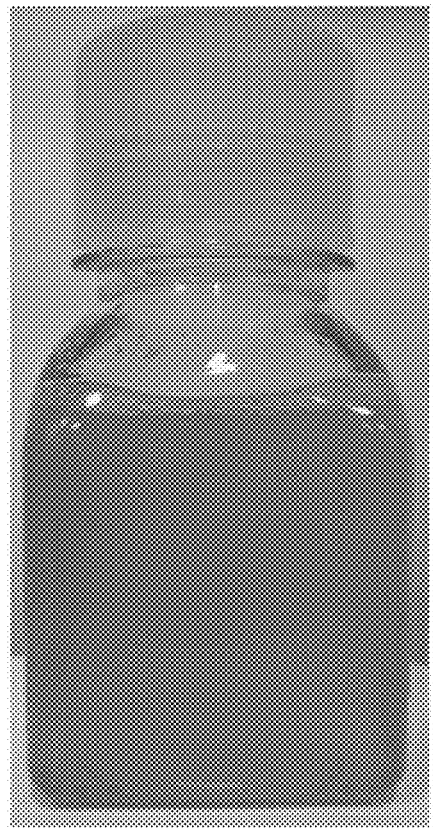
FIG. 11. Membrane Extracted Jellyfish Collagen (12 mg/ml)

The membrane based method achieved a yield of 0.185% based on the original catch weight of the jellyfish, signifying that 1 kg of jellyfish would yield 1.85 g of collagen. This yield makes the extraction of collagen much less time consuming and the quality of the scaffold was much higher, with a very distinct sponge like appearance as seen in FIG. 10. The process involved a one-week extraction protocol due to the condensing of cellulose diafiltration stages into a single day each rather than a period of 3 days by utilising the hollow fibre membrane filtration system described. This was much more effective and removed the need for centrifugation, and because of the scalable nature of the process, a single person can run a plant of any size, further increasing output. The downside to this process is an excess of γ-chain collagen which causes a turbid solution as seen in FIG. 11. This process at a 100 L scale as used in house produced 185 g per one batch run which meant 1850 electrospun scaffolds could be produced. This process would however still require the use of HFP to electrospin the collagen into a nano-fibrous scaffold.

Membrane Extraction—Bovine Insoluble Collagen

Figure 12:
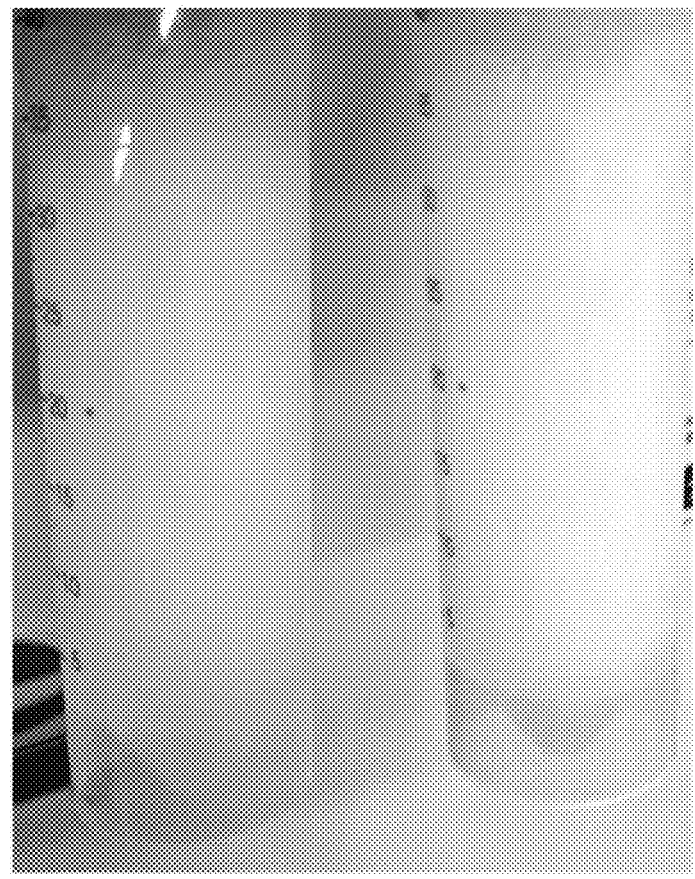
FIG. 12. Bovine Collagen Extract (15 mg/mL)

The insoluble bovine collagen which was extracted using the membrane extraction based method achieved a yield of 20% based on the original weight of the insoluble bovine material, signifying that 1 kg of insoluble bovine collagen would yield 200 g of soluble collagen. This yield makes the extraction of collagen much less time consuming and the quality of the scaffold was much higher, though the collagen appeared slightly more rigid in sponge form than the sponge like appearance of the jellyfish extract, however the bovine sponge had sufficient flexibility and was adequately compressible. The process involved a 5-day extraction protocol as above by utilising the hollow fibre membrane filtration system described without the need for NaOH treatment as this was carried out prior to material purchase. This was again much more effective by removing the need for centrifugation, and because of the scalable nature of the process, a single person can run a plant of any size, although this is dependent on the availability of insoluble collagen. This process at a 10 L scale as used in house started with 400 g which gave a total yield of 80 g of soluble collagen per one batch run which meant 800 electrospun scaffolds could be produced. This process would however still require the use of HFP to electrospin the collagen into a nano-fibrous scaffold and produces a very turbid solution with a large quantity of γ-chains as seen in FIG. 12.

Single Alpha Chain Collagens (SACCs) Isolation—all Species

The collagen monomers produced using this method showed good solubility, clarity and low viscosity at concentrations up to 10 mg/mL. When re-dissolved for electrospinning, the solution was a deep brown shade which was viscous enough to hold a droplet at the end of an 18 G needle however was noticeably lower than the same concentration of standard extract and was noticeably less opaque, suggesting increased solubility in the acetic acid-water mixture. The concentration was raised from 10% collagen to 25% to prevent spitting of single alpha chain collagen solution as was the case at 10% which was used previously.

Figure 13:
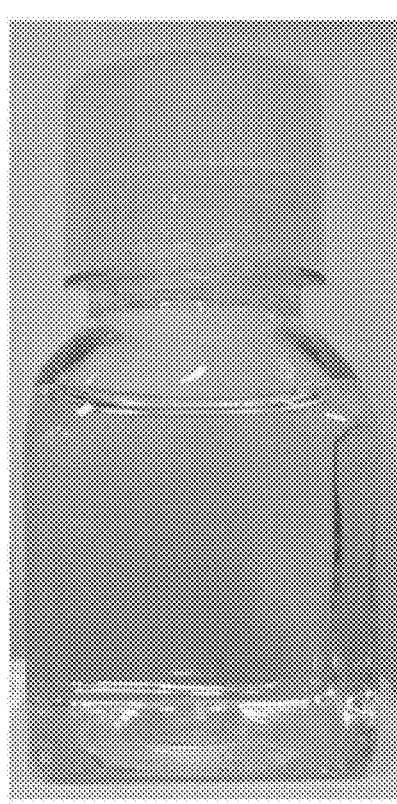
FIG. 13. SACCs (3 mg/ml)
Figure 14:
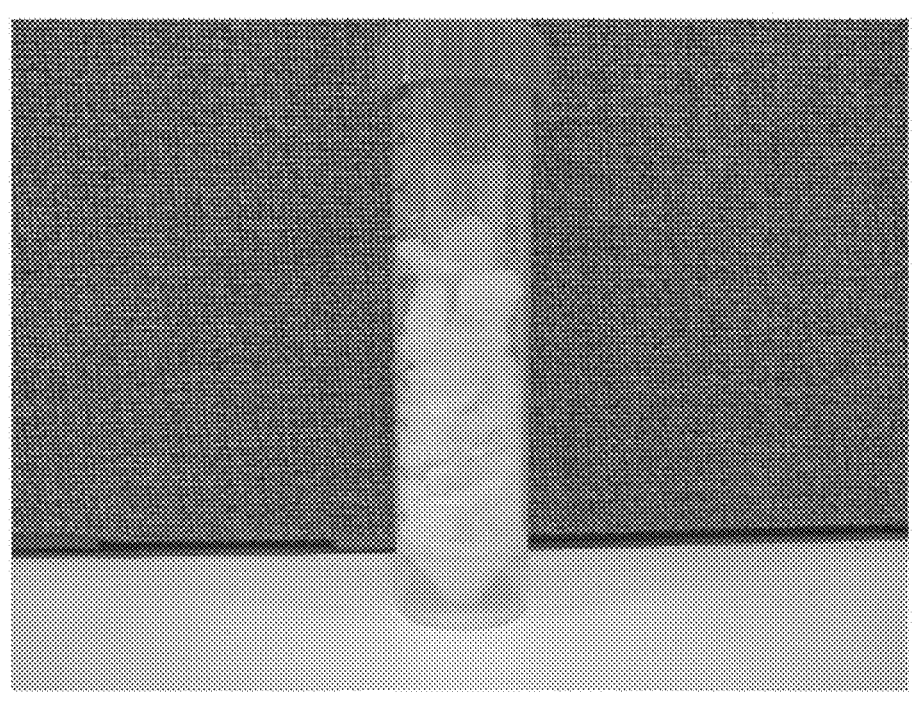
FIG. 14. Lyophilised SACCs Bovine Collagen.

For jellyfish SACCs isolation, the extraction used the 0.2 μm hollow fibre filtration and 50,000 NMWCO based method and achieved a yield of 12.5% based on the separation from the soluble collagen mixture, signifying that 1 kg of soluble bovine collagen would yield 125 g of SACCs. This yield makes the extraction of SACCs less efficient than that of the standard membrane extraction process, and the process involved a 10-day extraction protocol due to the added time of utilising the extra 0.2 μm and 50 000 NMCO hollow fibre membrane filtration steps described. This allowed for the effective removal of β and γ collagen chains and due to the nature of the process, a single person can run a plant of any size, further increasing output. This process at a 100 L scale as used in house produced 185 g of standard collagen which was processed to produce 23.1 g of SACCs per one batch run which meant 92 electrospun scaffolds could be produced. This process has the added benefit of not requiring the use of HFP to electrospin the collagen into nano-fibrous scaffolds, but instead can utilise a benign solvent such as acetic acid or a physiological buffer such as PBS. The solution produced was of very good clarity due to the absence of γ-chains as seen in FIG. 13 and produces a pure white powdered scaffold when lyophilised as seen in FIG. 14.

For bovine SACCs isolation, the SACCs which were extracted using the 0.2 μm hollow fibre filtration and 50,000 NMWCO based method achieved a yield of 10% based on the separation from the soluble collagen mixture, signifying that 1 kg of soluble bovine collagen would yield 100 g of SACCs. This yield makes the extraction of bovine SACCs less efficient than that of the standard membrane extraction process, and the process involved an 8-day extraction protocol due to the added time of utilising the extra 0.2 μm and 50 000 NMCO hollow fibre membrane filtration steps described. This allowed for the effective removal of β and γ collagen chains and due to the nature of the process, a single person can run a plant of any size, further increasing output, again dependent on the availability of insoluble collagen precursor. This process at a 10 L scale as used in house produced 80 g of standard collagen which was processed to produce 8 g of SACCs per one batch run which meant 32 electrospun scaffolds could be produced. This process and the use of the SACCs has the added benefit of not requiring the use of HFP to electrospin the collagen into nano-fibrous scaffolds, but instead can utilise a benign solvent such as acetic acid or a physiological buffer such as PBS.

SDS PAGE

SDS PAGE analysis of the collagen samples showed the distinctive collagen α1 & α2 bands at ~105 and ~92 kDa respectively; β chain expression as well as the presence of γ chains. These are shown in lanes 7-10 of FIG. 15.

Figure 15:
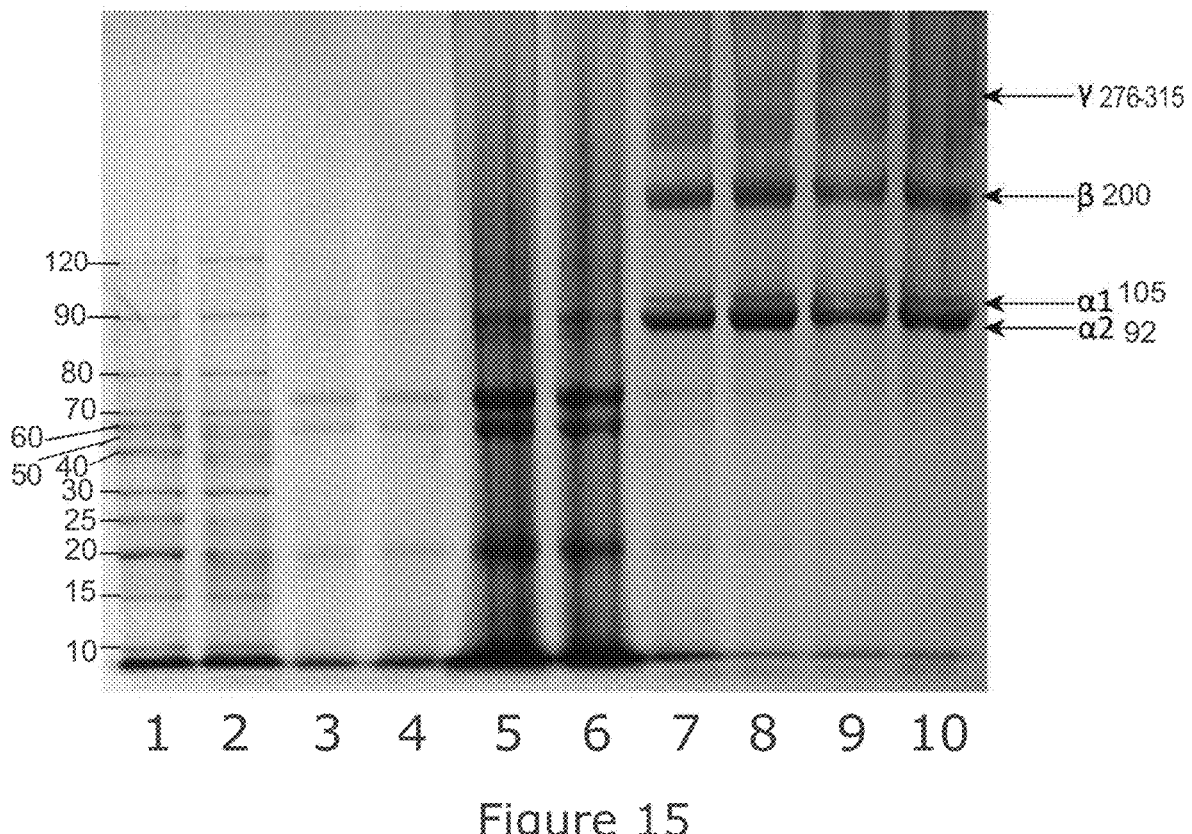
FIG. 15. SDS PAGE of collagen extracted from *Rhizostomas pulmo* showing collagen bands present in solution. Lanes 1&2: Benchmark High Molecular Weight Protein Ladder. Lanes 3-6: Non-Collagenous Proteins Removed from Solution During Extraction. Lanes 7-10: Collagen Solution Containing α1, α2, β & γ Collagen Chains.
Figures 16A, 16B:
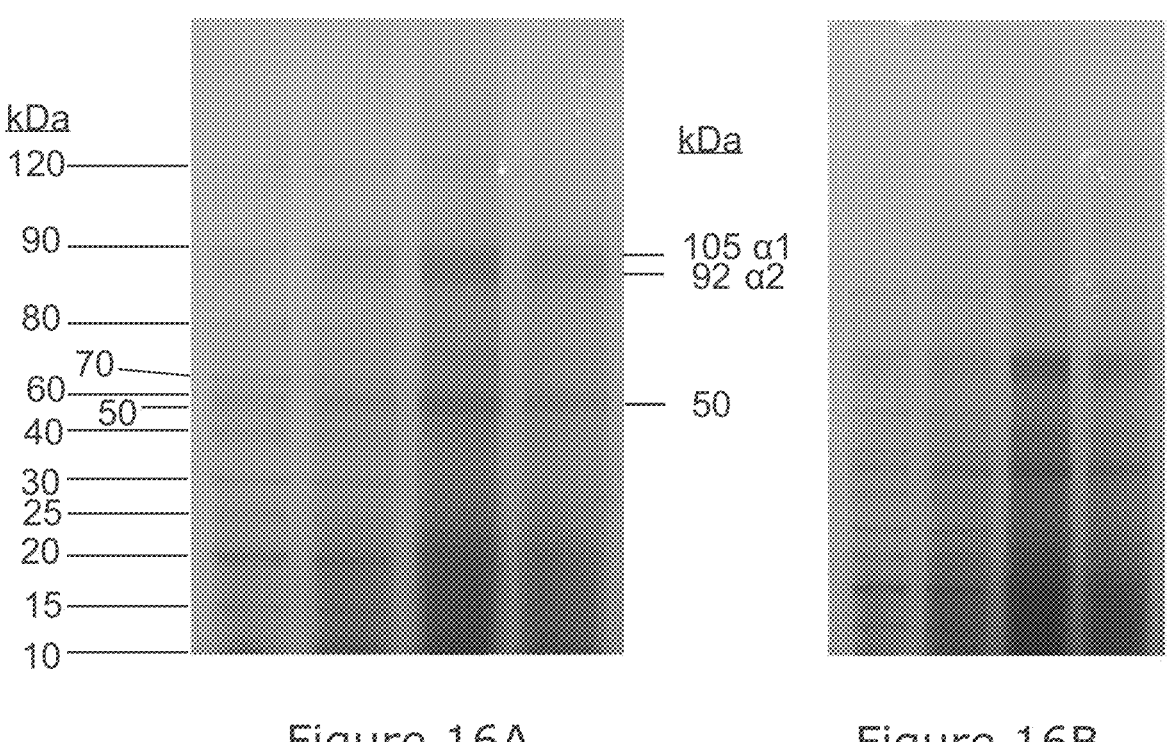
FIGS. 16A-16B.
Figure 33A:
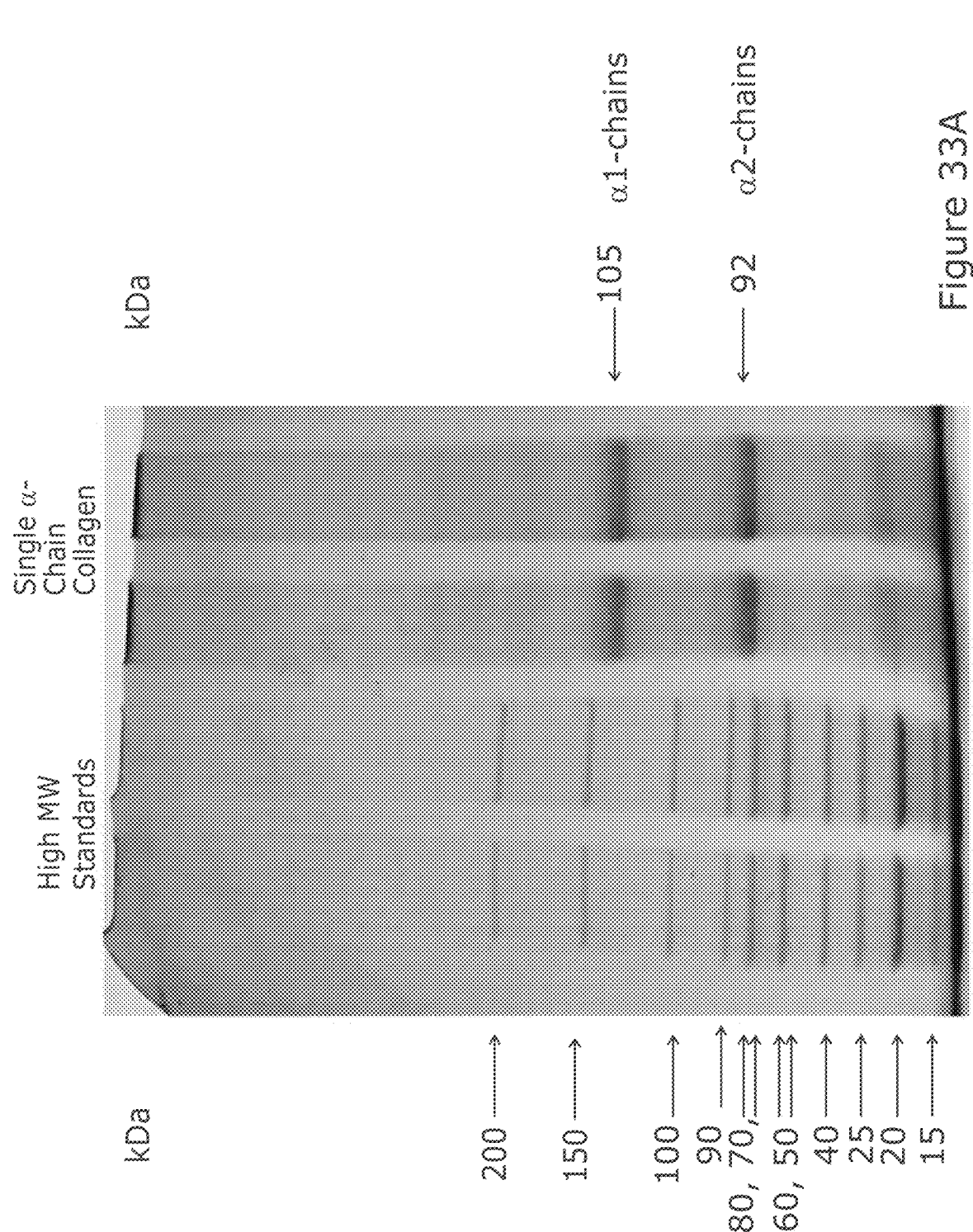
FIGS. 33A-33C. SDS page of extracted collagen comparing the composition of the acid soluble collagen (ASC) and samples of single alpha chain collagen (SACC).
Figure 33B:
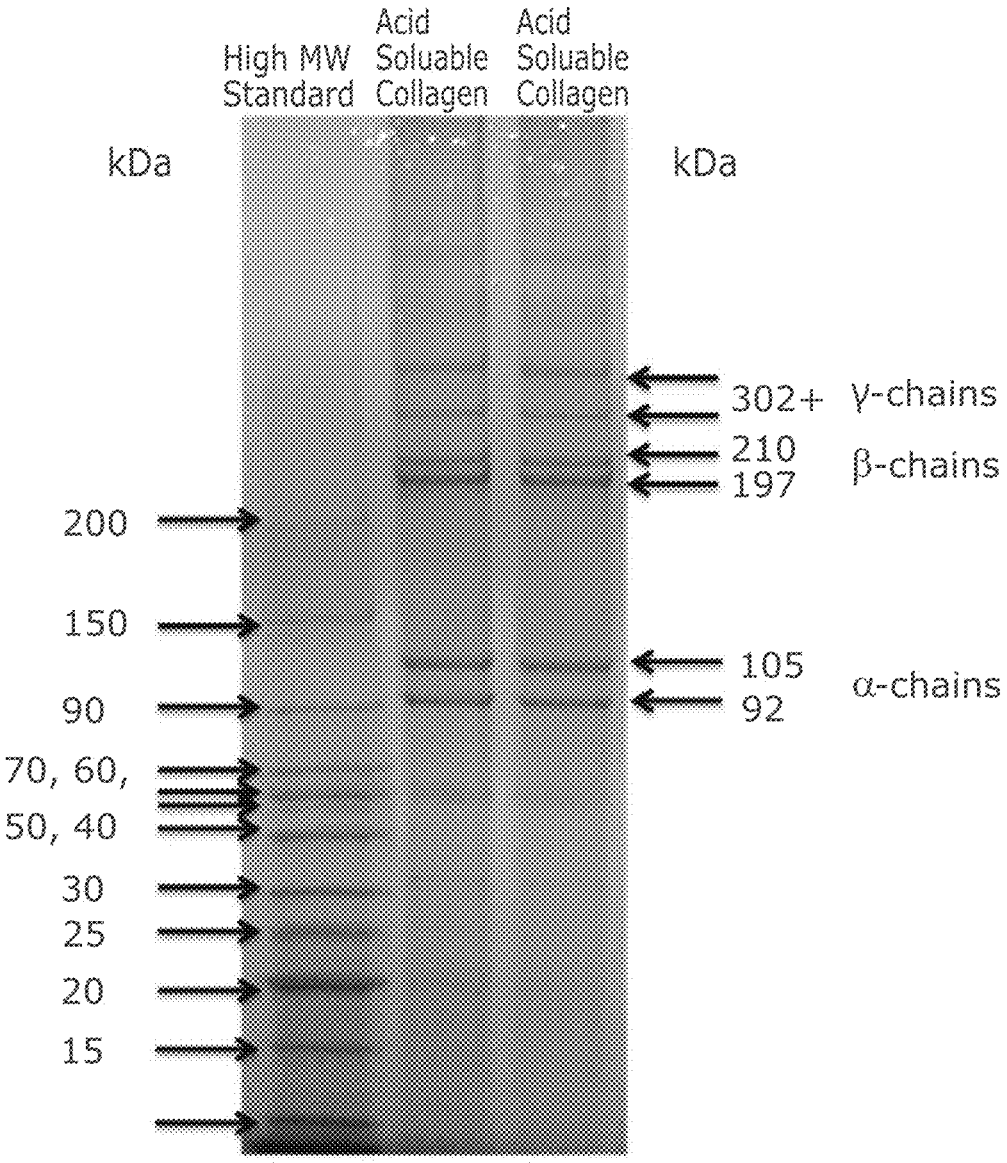
Figure 33C:
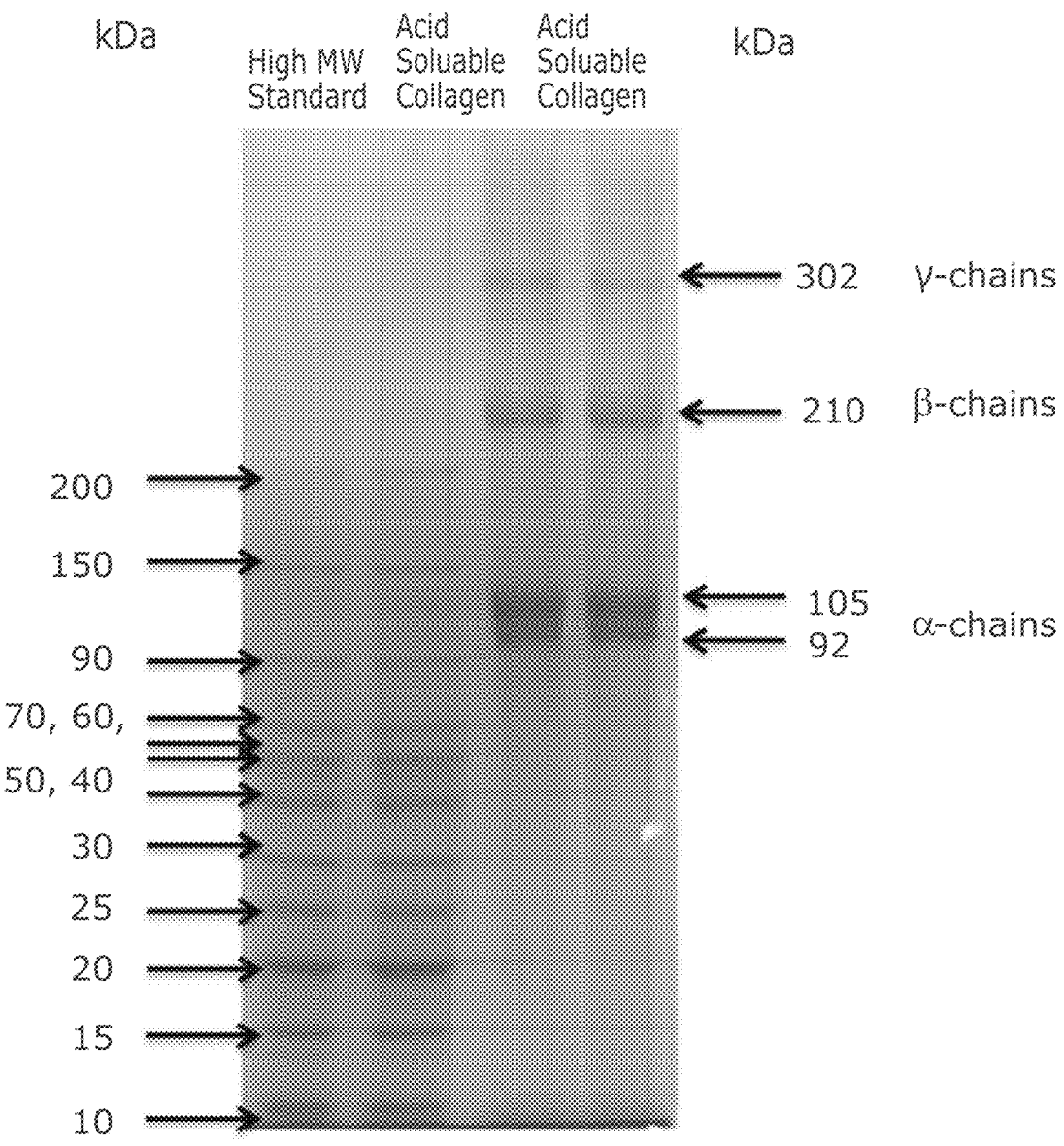

The jellyfish derived collagen that was examined using SDS PAGE showed the distinct α1 & α2 chains associated with acid solubilised collagen, as well as β and γ chains, which indicates the presence of both acid soluble collagen α1 & α2 chains, as well as a portion of semi-soluble collagen in solution which was not cleaved by digestion or removed when samples were centrifuged prior to testing for SDS PAGE. In order to isolate the α1 & α2 chains from the β and γ chains, crossflow filtration was utilised with a hollow fibre membrane of 0.2 μm nominal pore diameter. Once separation of sufficient quantity of α1 & α2 single alpha chain collagens was obtained and concentrated using a 50,000 NMWCO hollow fibre membrane, this was also examined using SDS PAGE analysis, as seen in FIG. 16a and FIG. 33a. This was then freeze dried in preparation for electrospinning. This showed distinct banding at ~92 and 105 kDa representing separated monomers of α1 & α2 collagens without the high abundance of β & γ chain collagens. This demonstrates the effective removal of high molecular weight collagens as desired while retaining α-chains used for electrospinning. The SDS PAGE shows a band present at approximately 40 kDa which was not removed in this instance due to insufficient cycles through the 50,000 NMWCO membrane cycle. This can be removed with added cycles of fresh AcOH into the solution and also aids in the removal of other background substances which are causing a haze to appear at the bottom of the gel. The collagen that was electrospun was re-dissolved in 0.5 M AcOH and tested; this can be seen in FIG. 16b. In contrast, however, standard acid soluble collagen comprises a mixed extract of alpha chain collagen but also contaminating higher molecular weight beta and gamma chains, which limits downstream utility (FIGS. 15 and 33b-c)

Electrospinning

Jellyfish Single Alpha Chain Collagens (SACCs) Electrospinning

Collagen was freeze dried using a primary drying shelf temperature of −30° C. for 70 h. Secondary drying was carried out with a shelf temperature of +20° C. for 15 h. Samples removed and placed in sealed containers showed that residual moisture for all experiments was between 2-5%.

The jellyfish SACCs were optimised as follows: 25% Collagen/AcOH solution electrospun at 18 kV, 20 cm and 0.35 ml/hour produced a constant droplet with a single taylor cone as shown in FIG. 17.

Figure 34:
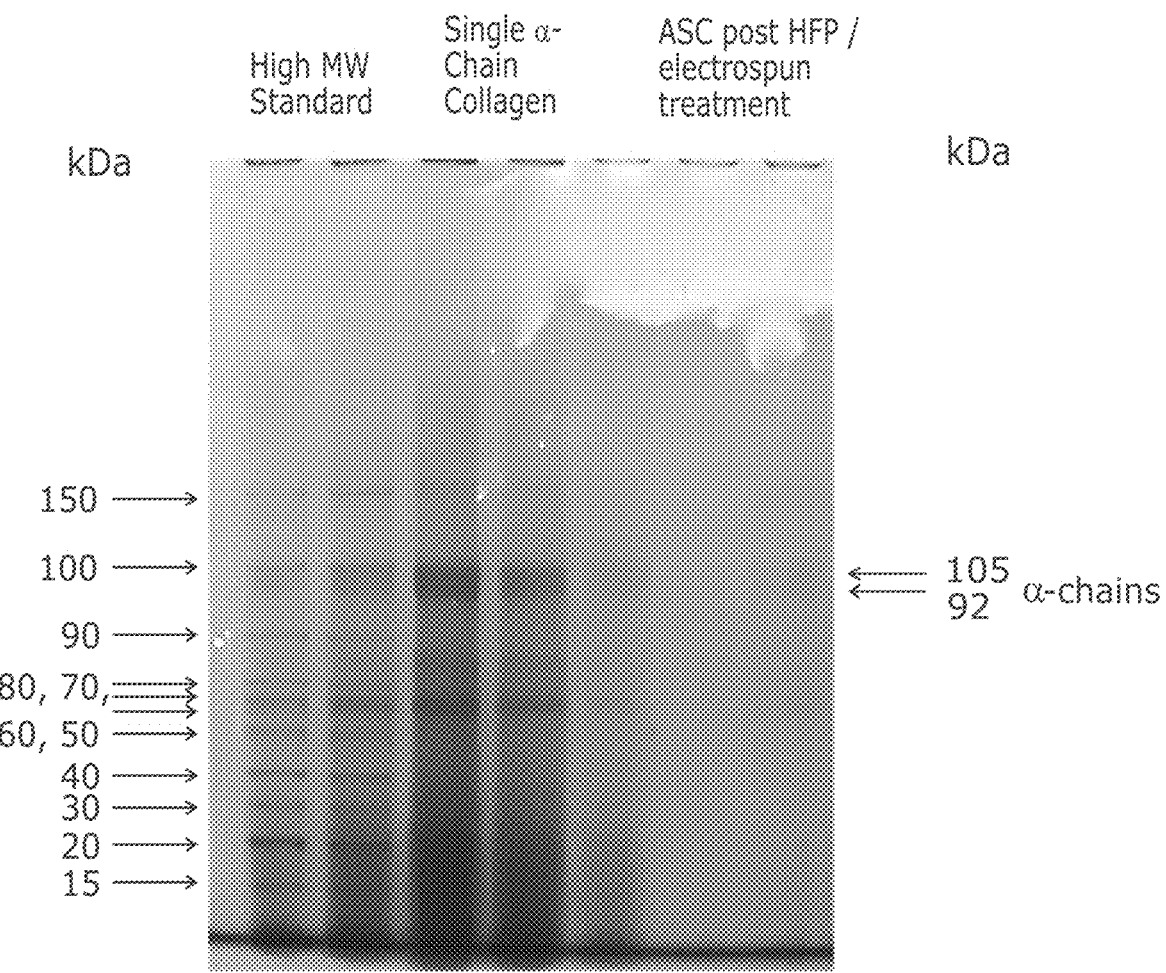
FIG. 34. SDS PAGE displaying single $\alpha$-chain collagen (SACC) post-electrospinning with the absence of high MW $\beta$ & $\gamma$ chains. In contrast, Acid soluble collagen can only be electrospun harsh solvents such as hexafluoropropanol (HFP) and as a consequence display very little remaining banding due to the chain breakdown caused by HFP.
Figures 35A, 35B, 35C, 35D, 35E:
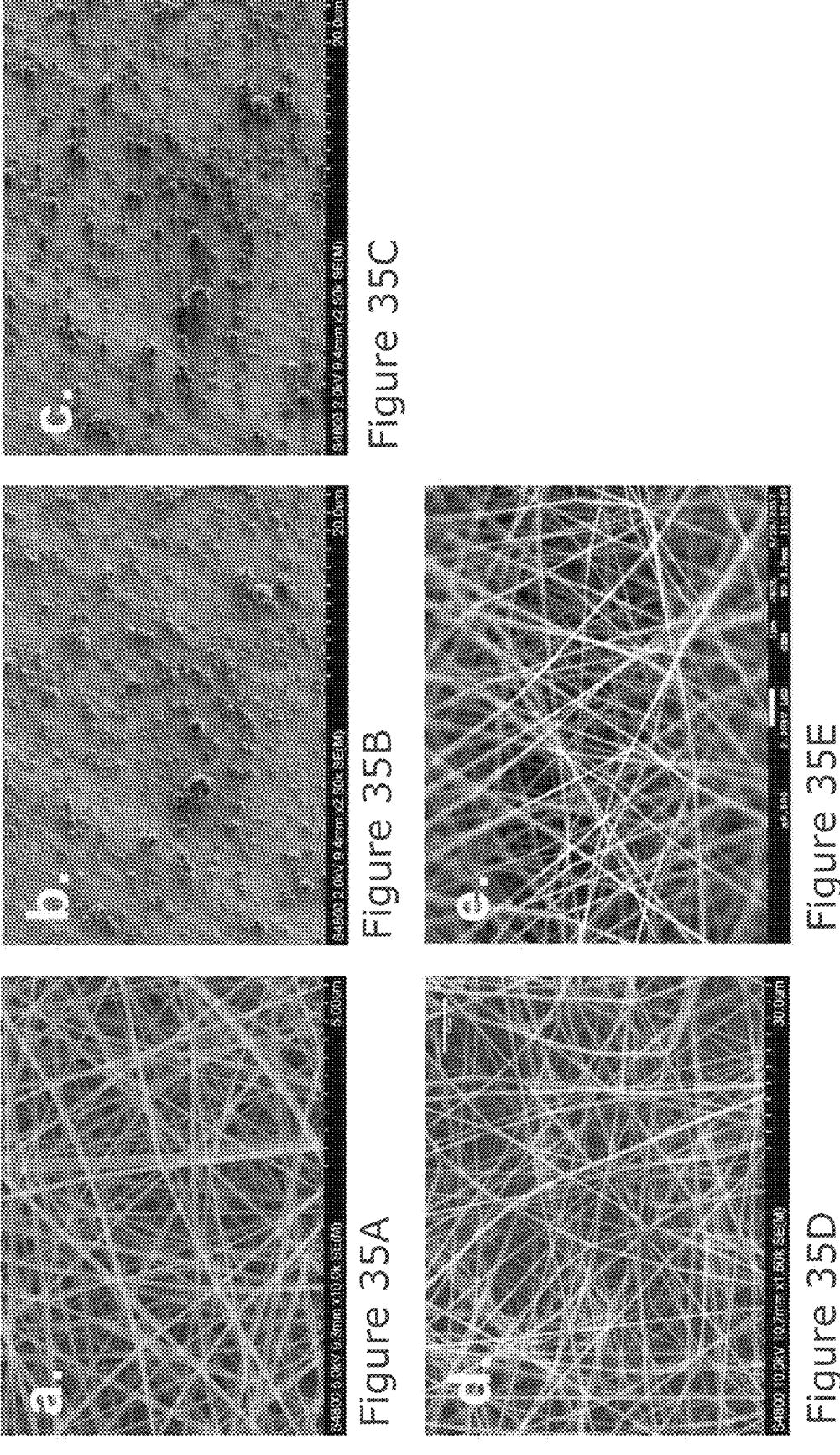
FIGS. 35A-35E. SEM micrograph of electrospun collagen comparing acid soluble collagen (ASC) and single alpha chain collagen (SACC) in different solvents.

The samples were examined under SEM and showed a mean fibre diameter of 646 nm with a standard deviation of 121 nm based on 90 fibre measurements. Micrographs of the needle electrospun fibres can be seen in FIG. 18a with frequency of range seen in FIG. 18b and FIG. 35d. In contrast, acid soluble collagen can only be electrospun in harsh denaturing solvents such as hexafluoropropanol (HFP) (FIG. 35a) and when electrospun in benign solvents such as acetic acid (FIG. 35b-c), in contrast to SACC, produces nanospheres due to the presence of high molecular weight beta and gamma chains. To this extent, electrospinning in harsher solvents destroys the chain structure and thus the ability of SACC to spin in benign solutions retains chain structure promoting its utility (FIG. 34).

Bovine Single Alpha Chain Collagens (SACCs) Electrospinning

Figure 20:
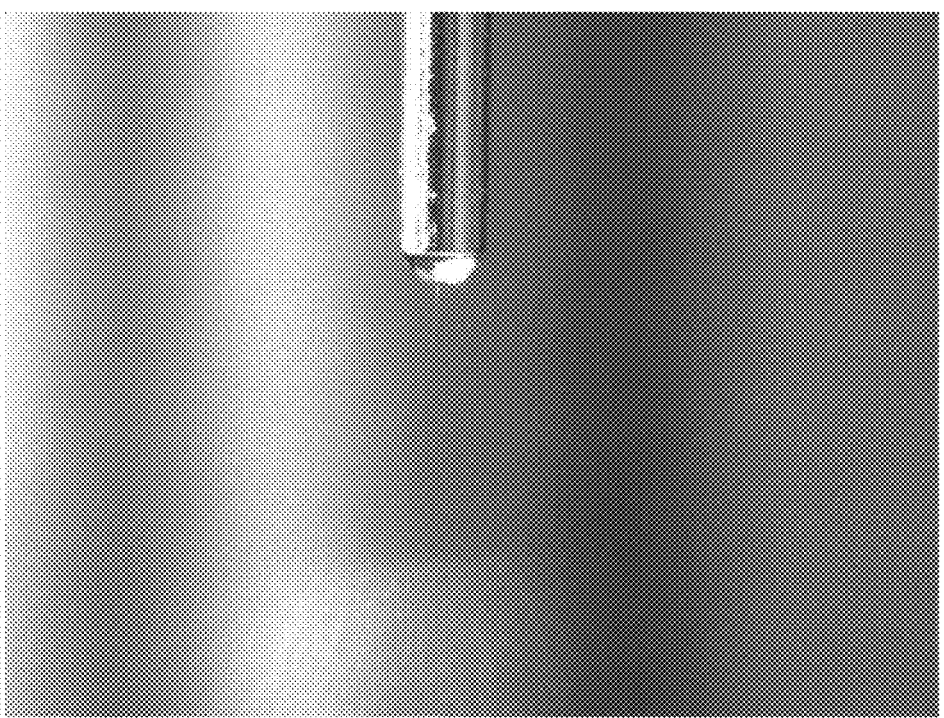
FIG. 20. Bovine SAC solution being electrospun with constant droplet replenishment and a single taylor cone producing a jet of collagen solution which lands on the grounding target as collagen nanofibers.

The bovine SACCs were optimised as follows: 35% Collagen/AcOH solution electrospun at 20 kV, 18 cm and 0.35 ml/hour produced a constant droplet with a single taylor cone as shown in FIG. 20.

Figure 21A:
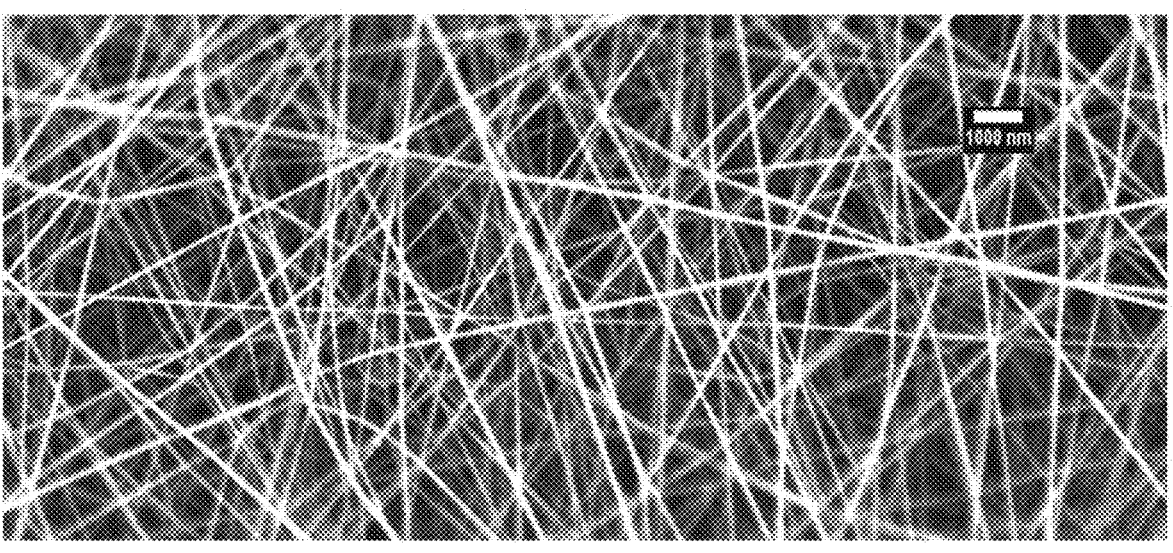
FIGS. 21A-21B.
Figure 21B:
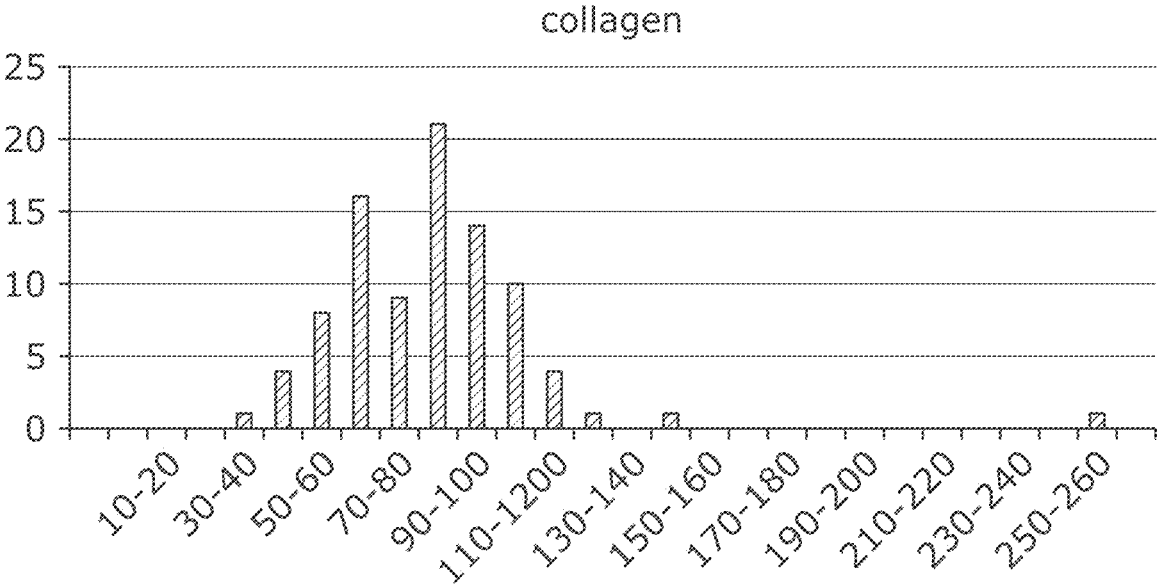

The samples were examined under SEM and showed a mean fibre diameter of 646 nm with a standard deviation of 121 nm based on 90 fibre measurements. Micrographs of the needle electrospun fibres can be seen in FIG. 21a and the frequency of range can be seen in FIG. 21b. Thus SACC can be obtained from multiple species as a source and retains the same properties.

Needle-Less Electrospinning

Figure 22A:
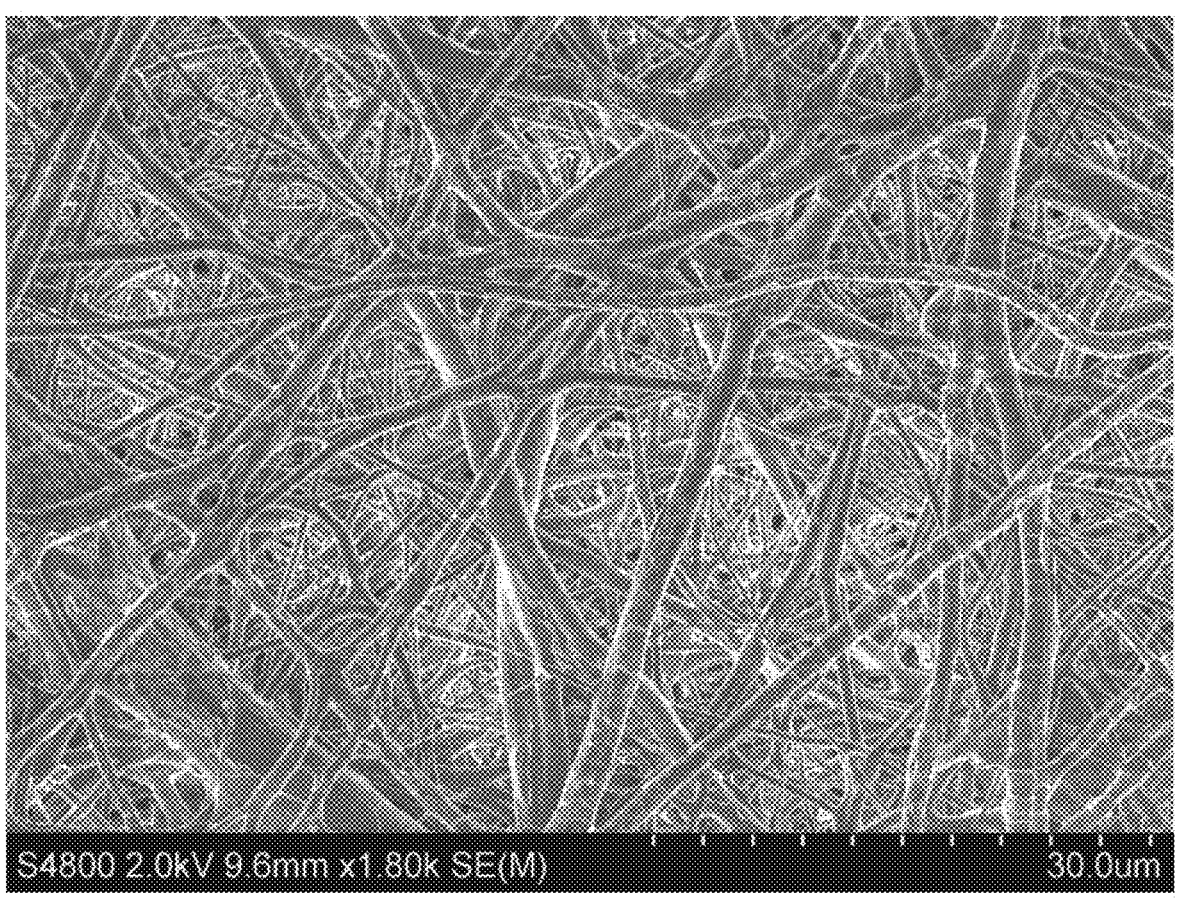
FIGS. 22A-22B.

Collagen was freeze dried using a primary drying shelf temperature of −30° C. for 70 h. Secondary drying was carried out with a shelf temperature of +20° C. for 15 h. Samples removed and placed in sealed containers showed that residual moisture for all experiments was between 2-5%. The jellyfish SACCs were optimised as follows: 25% Collagen/AcOH solution (90% AcOH in DI water) electrospun at 60 kV, 20 cm and 10 rotations/minute produced a collagen mat at a consistent rate. The samples were examined under SEM and showed a mean fibre diameter of 1128 nm with a standard deviation of 406 nm based on 90 fibre measurements. Micrographs of the needle-less electrospun fibres can be seen in FIG. 22a with frequency of range seen in FIG. 22b.

PBS Electrospinning of SACCs

Figure 23A:
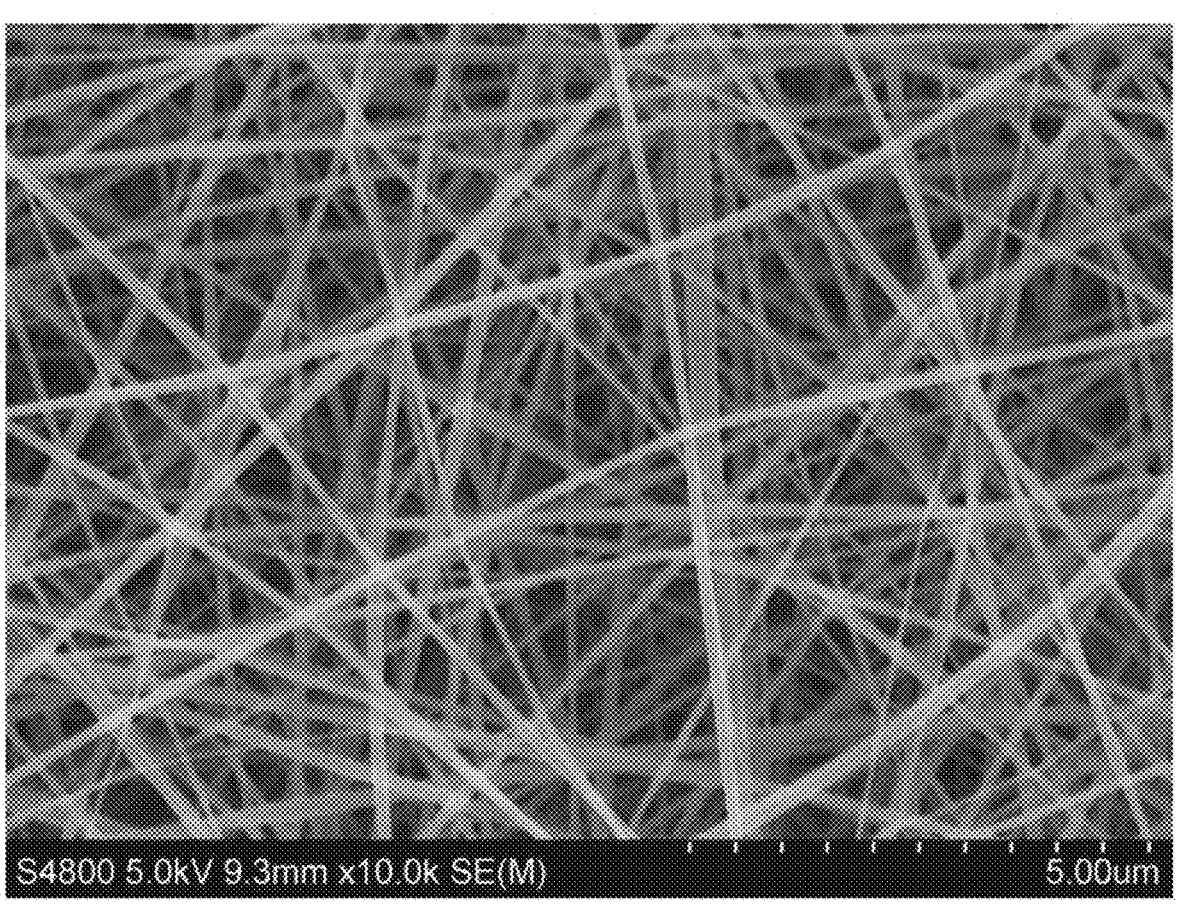
FIGS. 23A-23B.
Figure 23B:
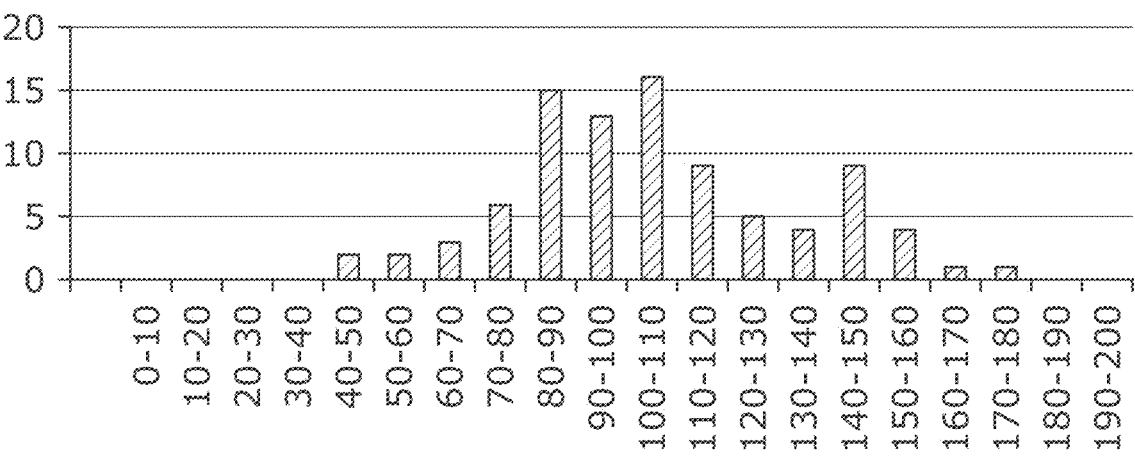

The SACCs which were dissolved in a standard PBS solution were more opaque than the acetic acid solution used above and appeared slightly more viscous. The concentration was optimised at 20% SACCs which gave a good fibre production without spitting of solution. Samples of collagen which were electrospun from a PBS formulation were examined under SEM and fibre diameter was shown to be 105 nm ±28 nm as shown in FIG. 23. SEM images can also be seen in FIG. 35e.

Crosslinking

EDC Crosslinking

Figure 24:
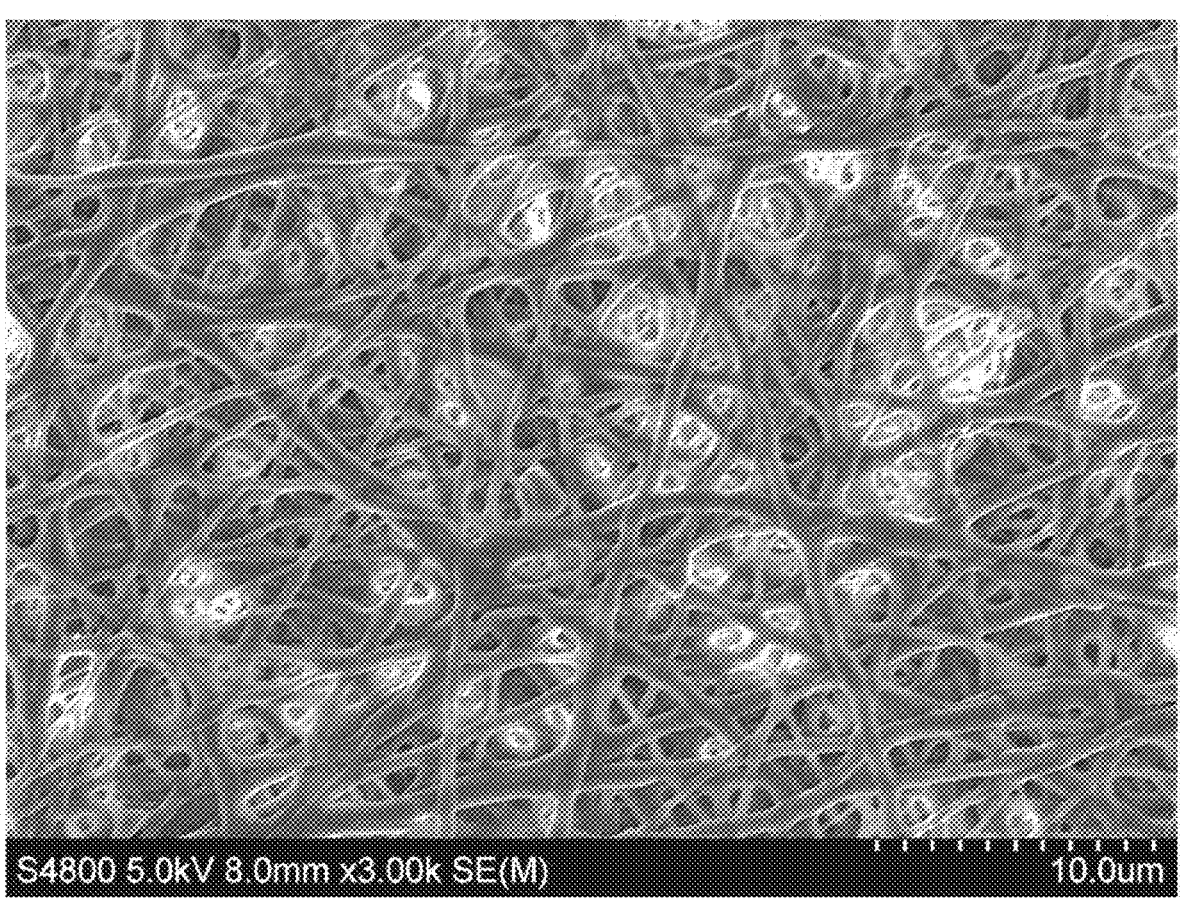
FIG. 24. SEM micrograph of jellyfish SACCs fibres electrospun and subsequently crosslinked using EDC.

Crosslinking of collagen fibres using a 1% EDC solution using our compression method yielded mats with little change from the original on the macro scale, SEM imaging was taken of the processed fibres as seen in FIG. 24 and fibre diameter was 125, with a standard deviation of 32 nm.

FTIR

Collagen samples were examined using a Perkin Elmer FTIR/ATR device using a soft tip. A small volume of solution was placed on the diamond stage and allowed to dry. The samples were then tested using a scan range from 4000-400 cm$^{-1}$. Once background correction was carried out, the data was normalised to 3 Absorbance units (A) at the average amide II peak of 1558 cm$^{-1}$ and was analysed using the Spectrum software which compared between samples to give a percentage similarity.

Figure 25:
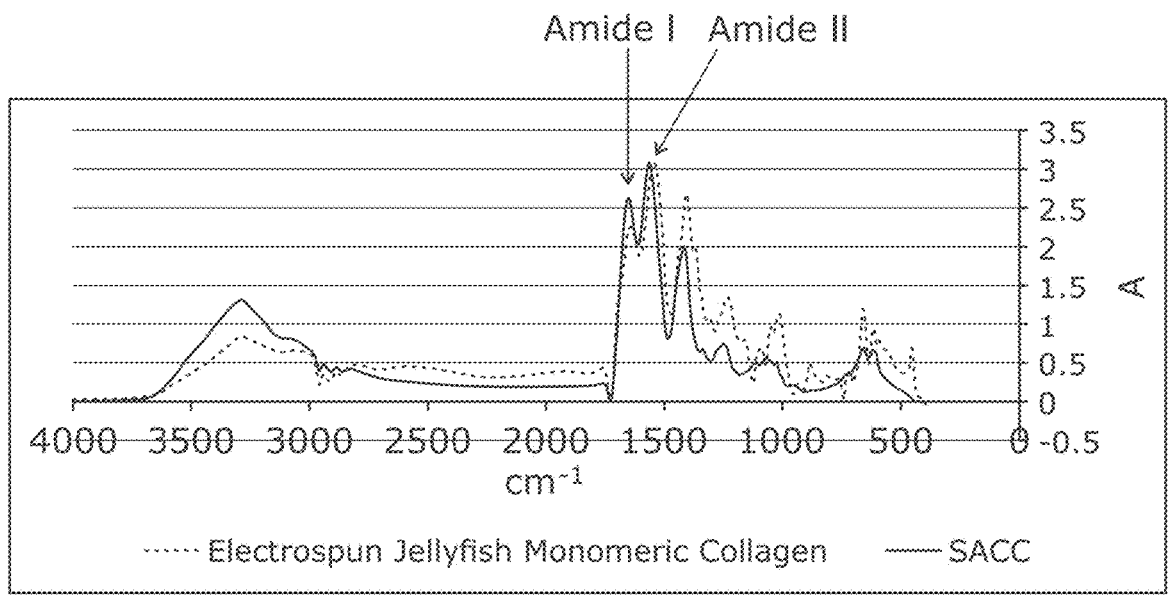
FIG. 25. Comparison of SACCs prior and post electrospinning; Electrospun samples show a reduction in the amide I peak representing a further reduction in any triple helical collagen content.
Figure 26:
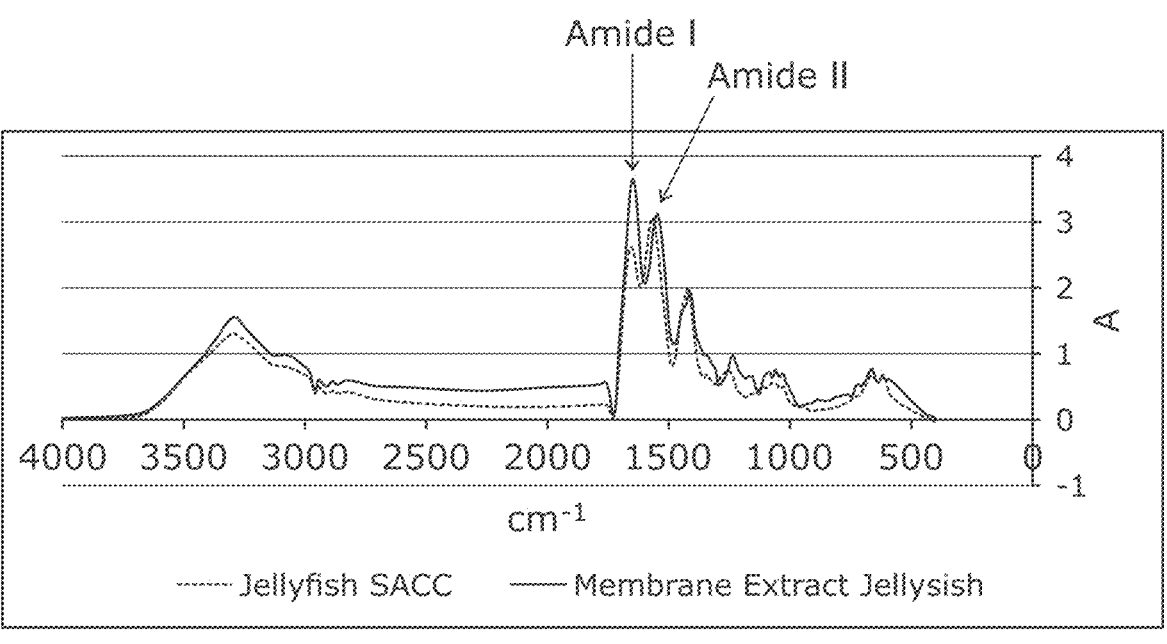
FIG. 26. Chart comparing SACCs and membrane extracted collagens to examine any differences in structure. All data was baseline corrected and normalised using Perkin Elmer Spectrum software at 1558 cm$^{-1}$. The SACCs displays a decrease in the amide 1 band region relative to the standard extraction sample, suggesting a reduction in triple helix presence at 1638 cm$^{-1}$; This correlates well with the SDS PAGE results, where the triple helical $\gamma$-chain collagens have been removed in SACCs samples.
Figure 27:
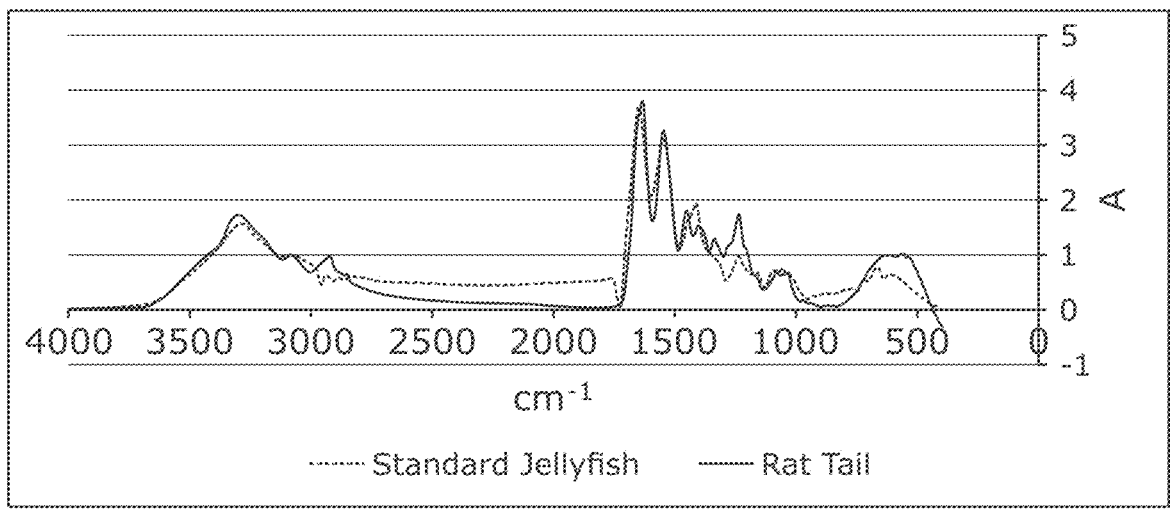
FIG. 27. FTIR Spectra comparing collagen extracted from jellyfish with rat tail collagen type I. Black spectra represents jellyfish collagen, red spectra represents rat tail collagen. Homology is 60.4%. This demonstrates that the membrane extracted jellyfish is not affected by the extraction process in comparison to classically extracted collagens such as rat tail.
Figure 28:
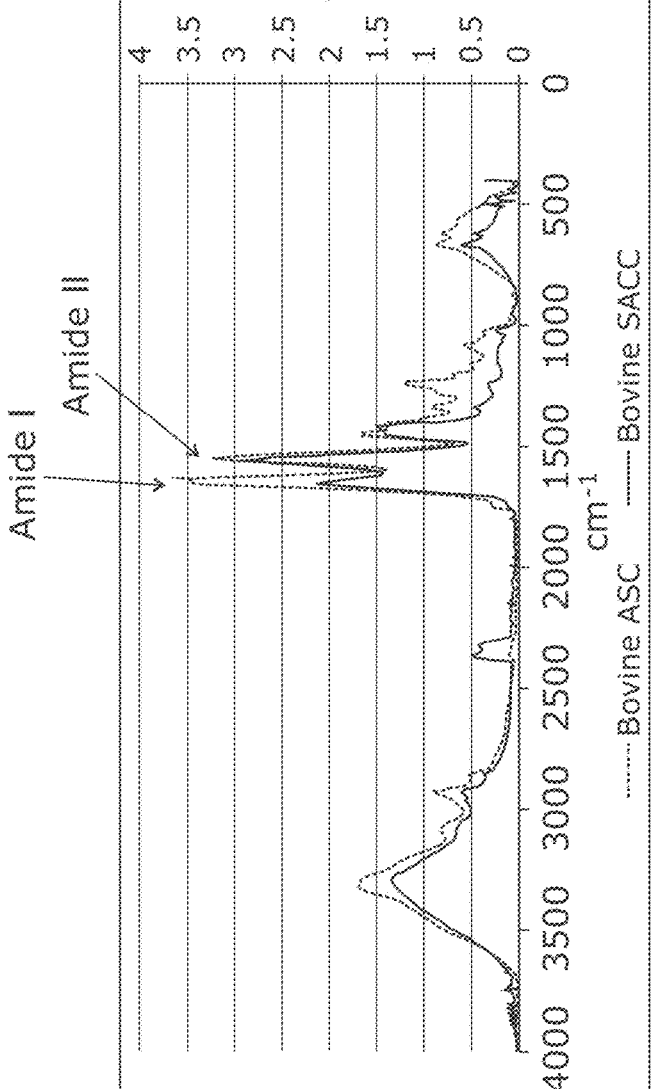
FIG. 28. FTIR Spectra comparing membrane bovine collagen extract with alpha chain bovine collagen. Black spectra represents alpha chain bovine collagen, blue spectra represents bovine collagen extracted using the membrane collagen. Homology is 21.8% with a large reduction in the amide I band; this amide I reduction demonstrates the large reduction in triple helical collagen present in the sample. As the standard bovine collagen was insoluble when purchased and underwent minimal processing for solubilisation, there remains a large fraction of $\beta$ & $\gamma$ chain collagens which is seen in FIG. 15. This clearly demonstrates a distinct separation from standard collagen extracts as the SACCs has a distinct FTIR absorbance pattern, sharing a homology of only 21.8% with the solution from which it is derived/separated. Thus, the FTIR spectra acts as a 'fingerprint' to the protein which is unique. [For 2 samples to be considered identical (such as in the production of paracetamol) a homology value >95% is required, making this a very selective process.]

The Findings of this work showed that by producing SACCs it was possible to obtain pure α1 & α2 chains which are not found to be naturally occurring. Their enhanced solubility raised questions as to whether the proteins had been partially denatured, However, FTIR examination of vibrations relating to secondary structure has demonstrated that the only significant change is a reduction in the amide 1 region due to the absence of triple helix (γ-chain collagens). This in turn causes a change in the ratio of amide 1 and amide 2, with amide 2 becoming the more pronounced peak, as seen in FIGS. 25 and 26.

Figure 22B:
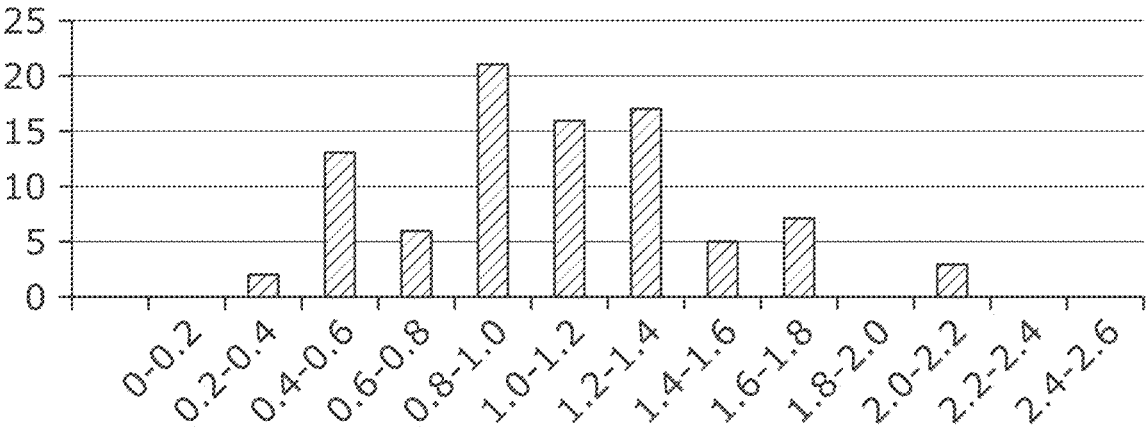

Collagen samples from base materials were tested against their electrospun counterparts and the percentage homology was examined. This data was also compared to rat tail type I collagen (Sigma, UK) to act as an external standard. The SACCs differed from standard collagen by a reduction in the triple helix absorption at 1638 cm$^{-1}$. The peaks of interest which were examined are listed in table 1. The comparisons of collagen in preceding and electrospun forms are shown in FIG. 22b All data was baseline corrected and normalised using Perkin Elmer Spectrum software at 1558 cm$^{-1}$.

The region representing the relative abundance of triple helix was reduced in SACCs samples and electrospun samples as expected due to the reduction in γ-chain abundance in the samples. Uncoiled, alpha helix, beta sheet secondary structured did not alter in ratios of abundance when the influence of the reduction of triple helix was accounted for; suggesting the secondary structure of the alpha chains has not been altered from the secondary structure of standard collagen samples as shown in FIG. 26.

Collagen Amino Acid Chain Modelling

Collagen solubility is an area which has been debated thoroughly in the literature; particularly ascertaining to electrospun scaffolds. We have demonstrated that SACCs are soluble in physiological buffers and benign solvents such as AcOH. To gain a better understanding of this increased solubility we examined the structure of collagen and the derivatives thereof.

Figure 29:
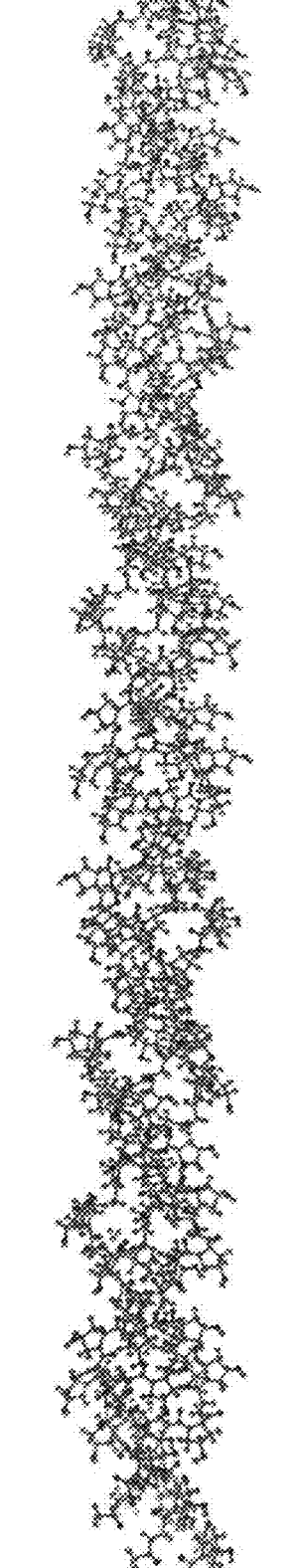
FIG. 29. Triple helix peptide of Gly-Pro-Hyp (Glycine-Proline-HydroxyProline) repeats arranged with a hybrid Lui Storey and Conjugate Descent optimisation (LS-CD) using Abalone software to build amino acid structure.
Figure 30:
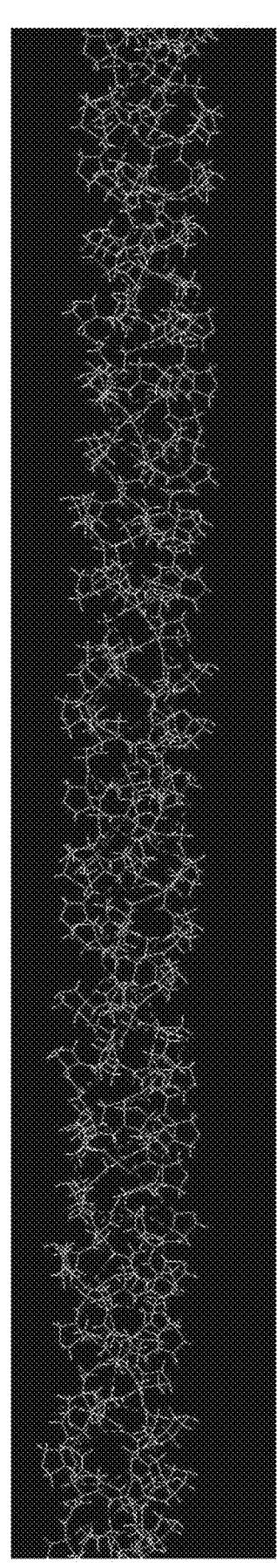
FIG. 30. Hydrogen bonding analysis between collagen chains is shown in green. The bonding sites face inward on the chains, preventing access to external bonding from water. These sites are exposed in single chain SACCs which lead to an increased solubility, allowing for dissolution in PBS and Hydrophillic solutions in single chain form which cannot be achieved with standard collagen while avoiding the negative attributes of gelatin extracts. Bonding site analysis produced using Zeus software.
Figure 31:
FIG. 31. Single chain peptide of Gly-Pro-Hyp repeats arranged with a hybrid Lui Storey and Conjugate Descent optimisation (LS-CD) using Abalone software to build amino acid structure.
Figure 32A:
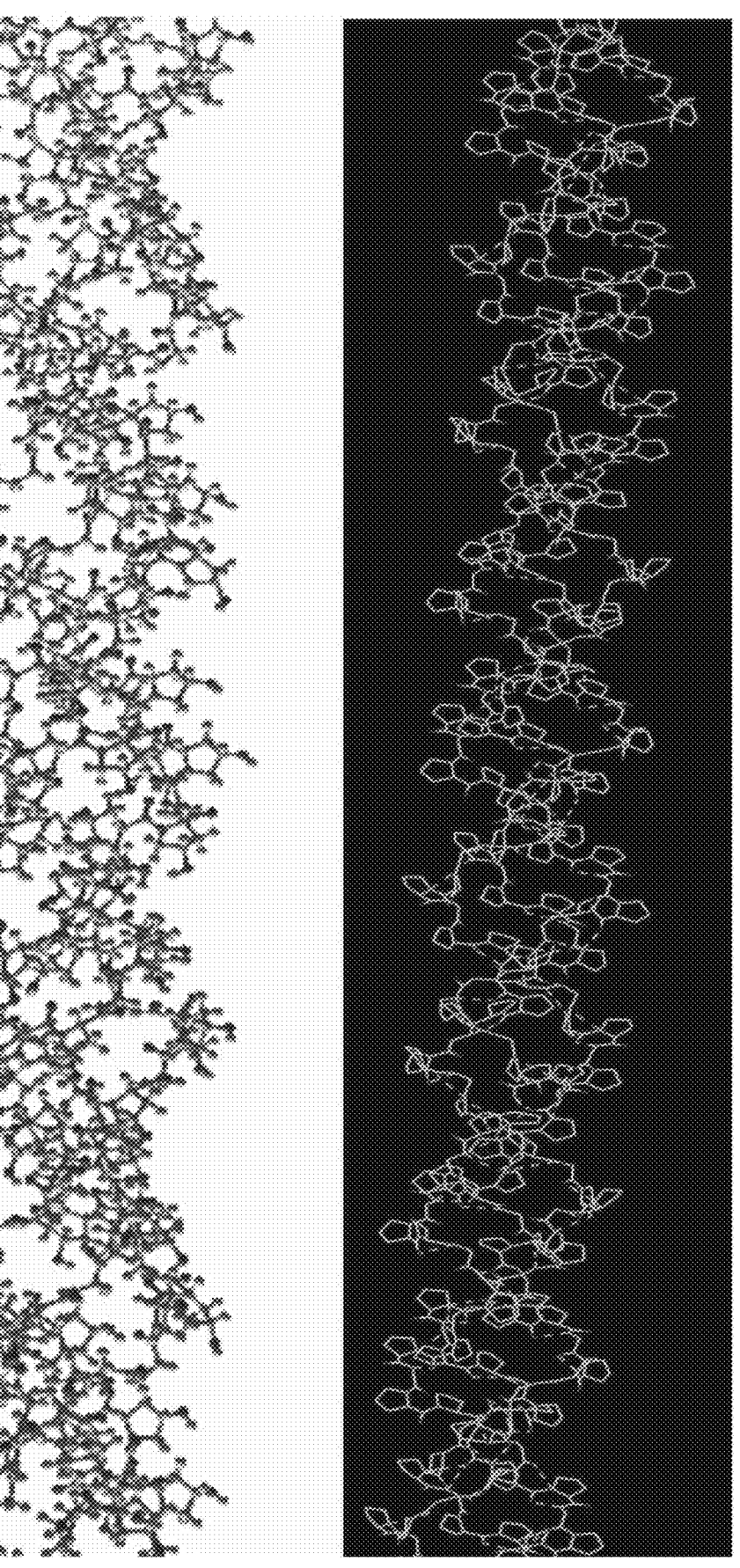
FIGS. 32A-32B. Molecular analysis of FIG. 32A: Acid Soluble Collagen (ASC)
Figure 32B:
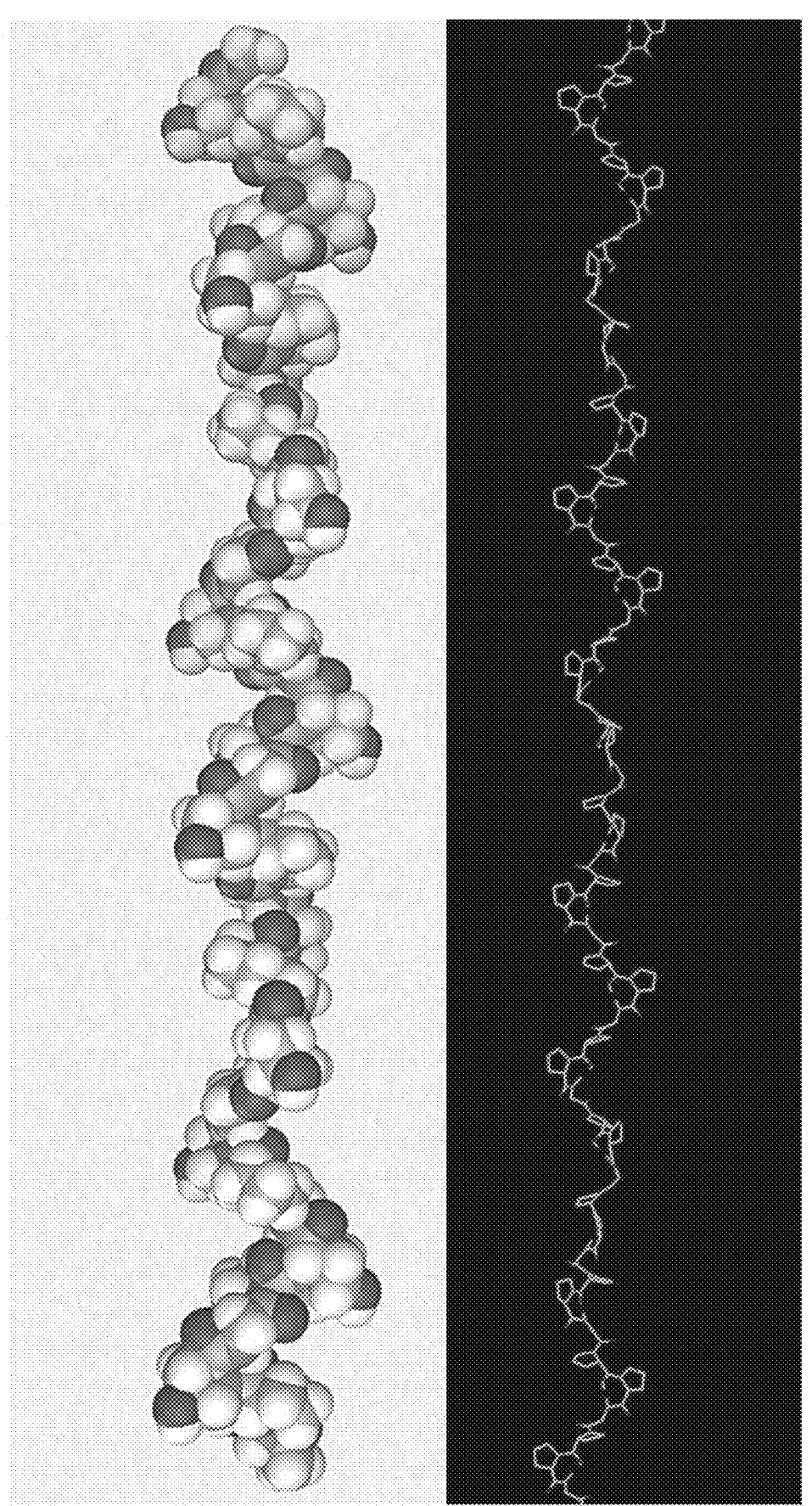

In order to assess why collagen in non-triple helix formation is able to dissolve readily we modelled the structure of collagen chains using the Abalone software to build a model protein sequence consisting of the Gly-X-Y repeat sequence; where X was Proline and Y was Hydroxyproline. This model was arranged with a hybrid Lui Storey and Conjugate Descent optimisation (LS-CD) as seen in FIG. 29 which was then exported into Zeus software and hydrogen bonding was examined between chains as seen in FIG. 30. The triple helical formation showed hydrogen bonding where possible occurred on the inward facing functional groups of amino acids which helped to stabilise the molecule. When the α-chains were separated from the triple helix molecule the SACCs, as shown in FIG. 31, had an abundance of hydrogen bonding sites which allow for increased solubility. This is further shown and modelled in FIG. 32. Based on this modelling, ASC has approximately 90 free hydrogen bonds per chain in contrast to approximately 530 free hydrogen bonds per chain of SACC.

This gives good evidence as to why the SACCs is both soluble and able to undergo electrospinning, with chains able to gain affinity to both the solvent and themselves during the electrospinning process.

SUMMARY

We have shown that by using a multi-step membrane separation process it is possible to produce SACCs and so obtain pure α1 &/or α2 chains, which are not found to be naturally occurring. These SACCs composed of α1 &/or α2 chains can be separated from the acid solubilised collagen mixture successfully giving rise to new opportunities for the use of this physiologically soluble collagen in applications such as wound aerosol sprays, which were not previously possible because of the insoluble nature of collagen in a suitable solvent system.

Further, by using less harsh isolation techniques, possible due to the alternative separation methodology, SACCs maintain their secondary structure and can be subsequently electrospun to produce nanofibrous mats which mimic native ECM conditions without the need to include a co-polymer component to allow electrospinning to occur. This solves the unmet need for collagen that can be formulated into physiological systems for applications ranging from injectables, implants, bio-active wound dressings as well as a suitable tissue engineering substrate. The creation of this unique polymer can give new life to the field of biomimetic scaffold production by introducing a pathway for its own use across different fields.

We have also demonstrated that collagen which contains the high molecular weight chains conforms to traditional use of HFP in collagen electrospinning in both mammalian and non-mammalian systems but demonstrates the time sensitivity of the solution produced. This therefore presents a promising finding for collagen electrospinning which allows the collagen formulation to be stored prior to electrospinning and can minimise wastage from scaffold production for an expensive product which is in great need. We have shown that the SACCs formulation works in a variety of organisms and show cross-species homology in both the production and electrospinning of the single alpha chain collagen chains.

TABLE 1

| Expected λ (±2 cm$^{-1}$) | Corresponding Vibration |
| --- | --- |
| 1690 | Parallel β-Sheets |
| 1680 | Anti-Parallel β-Sheets |
| 1668 | B-Turns |
| 1658 | A-Helix |
| 1647 | Unordered |
| 1638 | Triple Helix |
| 1625 | Parallel β-Sheets |
| 1612 | B-Turns |

TABLE 2

| Collagen Type | Approximate Length (Number of amino acids) | | |
| --- | --- | --- | --- |
| | α1 | α2 | α3 |
| 1 | 1464 | 1366 | |
| 2 | 1487 | | |
| 3 | 1466 | | |
| 5 | 1838 | 1499 | 1745 |
| 24 | 1714 | | |
| 26 | 3051 | | |

REFERENCES

Burke, L., Mortimer, C. J., Curtis, D. J., Lewis, A. R., Williams, R., Hawkins, K., . . . Wright, C. J. (2017). In-situ synthesis of magnetic iron-oxide nanoparticle-nanofibre composites using electrospinning. Materials Science and Engineering C, 70, 512-519. https://doi.org/10.1016/j.msec.2016.09.014

Neuhoff, V., Arold, N., Taube, D., & Ehrhardt, W. (1988). Improved staining of proteins in polyacrylamide gels including isoelectric focusing gels with clear background at nanogram sensitivity using Coomassie Brilliant Blue G250 and R250. ELECTROPHORESIS, 9(6), 255-262. https://doi.org/10.1002/elps.1150090603

Schneider, C. A., Rasband, W. S., & Eliceiri, K. W. (2012). NIH Image to ImageJ: 25 years of image analysis. Nat Meth, 9(7), 671-675. Retrieved from http://dx.doi.org/10.1038/nmeth.2089

Brodsky B., Ramshaw J. A. (1997) The collagen triple-helix structure. Matrix Biol. 15, 545-554 CrossRefMedlineGoogle Scholar Kielty C. M., Grant M. E. (2002) The Collagen family: structure, assembly and organization in the extracellular matrix. In Connective Tissue and Its Heritable Disorders: Molecular, Genetic, and Medical Aspects (Royce P. M., Steinmann B., eds) 2nd Ed., pp. 158-222, Wiley-Liss, New York Google Scholar Veit G., Kobbe B., Keene D. R., Paulsson M., Koch M., Wagener R. (2006) Collagen XXVIII, a novel von Willebrand Factor A domain-containing protein with many imperfections in the collagenous domain. J. Biol. Chem. 281, 3494-3504 Abstract/FREE Full Text Shoulders M. D., Raines R. T. (2009) Collagen structure and stability. Annu. Rev. Biochem. 78, 929-958 CrossRefMedlineGoogle Scholar

The invention claimed is:

1. A method for producing or purifying a single alpha chain collagen (SACC), the method consisting of the following steps:
   a) obtaining an extraction of collagen in alkaline solution;
   b) filtering the extraction of collagen in alkaline solution using at least one first filter membrane having a Nominal Molecular Weight Cut-Off (NMWCO) in the range of 1-100,000 Da to produce a first filter retentate;
   c) adjusting the pH of the first filter retentate to a pH of less than 3, thereby at least partially solubilising the collagen bound by the first filter retentate and filtering the at least partially solubilised first filter retentate until a pH of greater than 6 is achieved using said at least one first filter membrane to produce a second filter retentate;
   d) adjusting the pH of the second filter retentate so that it is acidic, thereby solubilising the collagen bound by the second filter retentate; and
   e) filtering the second filter retentate using at least one second filter membrane wherein the at least one second filter membrane is a micro-porous membrane comprising a pore size between about 0.05 to 2 μm and every 0.01 μm integer therebetween to produce a first filtrate comprising SACC;
   wherein the SACC comprises a single chain polypeptide existing as an alpha helix and having a molecular weight of approximately 100 kDa, a repeating sub structure of Glycine-X-Y, wherein X is any amino acid and Y is proline or hydroxyproline, non-helical N-terminal and/or C-terminal end, wherein the SACC does not comprise gamma collagen or beta collagen; and
   wherein said first filtrate contains an amount of SACC per total collagen protein content of at least 90% and comprises SACC at a concentration of at least 85% w/v.

2. The method according to claim 1, wherein the at least one first filter membrane has a NMWCO of 10,000 Da.

3. The method according to claim 1, wherein the extraction of collagen in alkaline solution in step a) is obtained by treating a collagen-containing sample with an alkaline or basic solution to allow cellular matter and other non-collagenous material to be destroyed.

4. The method according to claim 1, wherein in step b) the extraction of collagen in alkaline solution is filtered until a pH of less than 8 is achieved and the first filter retentate is obtained.

5. The method according to claim 1, wherein in step b) the first filter retentate is supplemented, before during or after filtering, with deionised water and/or in step c) the second filter retentate is supplemented with deionised water.

6. The method according to claim 1, wherein step c) is repeated at least once to improve yield and purity.

7. The method according to claim 1, wherein step c) is performed in a closed circulatory system that either runs constantly or runs constantly during the performance of the said specified steps.

8. The method according to claim 1, wherein said filtering in steps b), c), e) is comprises dialysis.

9. The method according to claim 1, wherein in step e) the first filtrate is filtered until a pH of less than 8 is achieved.

10. The method according to claim 1, wherein said extraction of collagen is obtained from mammalian or cnidarian tissue.

11. The method according to claim 1, wherein the at least one first filter membrane has a NMWCO of 50,000 Da.

\* \* \* \* \*